United States Patent
Lee et al.

(10) Patent No.: US 11,648,291 B2
(45) Date of Patent: May 16, 2023

(54) METHOD OF USING PRD, PRD-S TAD, ZF7 PEPTIDE OR MIXTURE THEREOF TO INHIBIT CELLULAR RESPONSE TO INFLAMMATORY STIMULI OR TREAT CYTOKINE-STORM-MEDIATED DISEASES

(71) Applicant: GUANGZHOU MEDICAL UNIVERSITY, Guangzhou (CN)

(72) Inventors: Jongdae Lee, Guangzhou (CN); Fengyuan Yang, Guangzhou (CN); Liya Shen, Luohe (CN); Dengxia Fan, Guangzhou (CN)

(73) Assignee: GUANGZHOU MEDICAL UNIVERSITY, Guangzhou (CN)

( * ) Notice: Subject to any disclaimer, the term of this patent is extended or adjusted under 35 U.S.C. 154(b) by 0 days.

(21) Appl. No.: 17/391,063

(22) Filed: Aug. 2, 2021

(65) Prior Publication Data
US 2022/0160826 A1 May 26, 2022

(30) Foreign Application Priority Data
Nov. 23, 2020 (CN) .......................... 202011323140.4

(51) Int. Cl.
| | | |
|---|---|---|
| *A61K 38/10* | (2006.01) | |
| *A61K 38/16* | (2006.01) | |
| *A61K 38/17* | (2006.01) | |
| *A61P 37/06* | (2006.01) | |

(52) U.S. Cl.
CPC .......... *A61K 38/1709* (2013.01); *A61K 38/10* (2013.01); *A61K 38/16* (2013.01); *A61P 37/06* (2018.01)

(58) Field of Classification Search
CPC ..... A61K 38/1709; A61K 38/10; A61K 38/16
See application file for complete search history.

(56) References Cited

PUBLICATIONS

Tang et al., "Cytokine Storm in COVID-19:The Current Evidence and Treatment Strategies", Frontiers in Immunology, 2020, pp. 1-13 (Year: 2020).*

* cited by examiner

*Primary Examiner* — Lianko G Garyu
(74) *Attorney, Agent, or Firm* — Muncy, Geissler, Olds & Lowe, P.C.

(57) ABSTRACT

The disclosure discloses a method of using PRD, PRD-S, TAD, ZF7 peptide or a mixture thereof to inhibit a cellular response to inflammatory stimuli or treat cytokine-storm-mediated diseases. An amino acid sequence of the PRD peptide is SEQ ID NO: 1, an amino acid sequence of the PRD-S peptide is SEQ ID NO: 2, an amino acid sequence of the TAD peptide is SEQ ID NO: 3, and an amino acid sequence of the ZF7 peptide is SEQ ID NO: 4.

13 Claims, 24 Drawing Sheets
Specification includes a Sequence Listing.

```
                            SEQUENCE LISTING

<160> NUMBER OF SEQ ID NOS: 41

<210> SEQ ID NO 1
<211> LENGTH: 30
<212> TYPE: PRT
<213> ORGANISM: Homo sapiens

<400> SEQUENCE: 1

Gly Gln Pro Pro Ser Gln Pro Pro Gln Gly Gln Gly Pro Pro Ser Gly
1               5                   10                  15

Pro Gly Gln Pro Ala Pro Ala Ala Thr Gln Ala Ala Pro Gln
            20                  25                  30

<210> SEQ ID NO 2
<211> LENGTH: 15
<212> TYPE: PRT
<213> ORGANISM: Homo sapiens

<400> SEQUENCE: 2

Gln Pro Pro Gly Gln Gly Pro Pro Ser Gly Pro Gly Gln Pro Ala
1               5                   10                  15

<210> SEQ ID NO 3
<211> LENGTH: 20
<212> TYPE: PRT
<213> ORGANISM: Homo sapiens

<400> SEQUENCE: 3

Arg Gln Ala Met Arg Ile Asn Ile Asn Pro Ser Thr Ala Asn Ser Pro
1               5                   10                  15

Lys Cys Gln Glu
            20

<210> SEQ ID NO 4
<211> LENGTH: 34
<212> TYPE: PRT
<213> ORGANISM: Homo sapiens

<400> SEQUENCE: 4

Pro Pro Lys Gln Arg Cys Arg Ala Pro Ala Cys Asp His Phe Gly Asn
1               5                   10                  15

Ala Lys Cys Asn Gly Tyr Cys Asn Glu Cys Tyr Gln Phe Lys Gln Met
            20                  25                  30

Tyr Gly

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
caactttgac tgctgtcttg gata                                          24

<210> SEQ ID NO 6
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 6 ttgactttttt tactgaggag acgc                                         24

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
cttggcagcc ttcctgattt                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ttccttgggg tccagacaga                                               20

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
atcaccatct tccaggagcg ag                                            22

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 10
gggcagagat gatgacccctt ttg                                          23

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
gtggcattca aggagtacct c                                             21

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
```

```
tgatggcctt cgattctgga tt                                              22

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 13
actcacctct tcagaacgaa ttg                                             23

<210> SEQ ID NO 14
<211> LENGTH: 23
<212> TYPE: DNA
<213> ORGANISM: Artificial Sequence
<220> FEATURE:
<223> OTHER INFORMATION: CCATCTTTGGAAGGTTCAGGTTG

<400> SEQUENCE: 14
ccatctttgg aaggttcagg ttg                                             23

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
cggcagattc cacagaattt c                                               21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
aggtcgctga catatttctg g                                               21

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
taagtgcgat tgtacccgga c                                               21

<210> SEQ ID NO 18
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 18
tttgtagcca tagtcagcat tgt                                             23

<210> SEQ ID NO 19
<211> LENGTH: 20
<212> TYPE: DNA
<213> ORGANISM: Artificial Sequence
```

-continued

<220> FEATURE:
<223> OTHER INFORMATION: Synthetic oligonucleotide

<400> SEQUENCE: 19
gcaatcaatg ccccagtcac                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tgcttgtcca ggtggtccat                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gaaggtcctc tctgatgaca                                                    20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
aagtagagga gtgagctctg                                                    20

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 23
ccctcgtttt gccatgaac                                                     19

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
gttgctgctg gttggagttg                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gcctccagga tgttaccagg                                                    20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
ggcctctgct gtagtccttt                                              20

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
gacaucuucu ggucagagat t                                            21

<210> SEQ ID NO 28
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 28
ucucugacca gaagauguc                                               19

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
ccctgcgggg gctgcgaagg                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
acccgggcaa ccggcacccg                                              20

<210> SEQ ID NO 31
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 31
aaaagacatc ttctggtcag agattggatc caatctctga ccagaagatg tc          52

<210> SEQ ID NO 32
<211> LENGTH: 23
<212> TYPE: DNA
<213> ORGANISM: Artificial Sequence
<220> FEATURE:
<223> OTHER INFORMATION: Synthetic oligonucleotide

```
<400> SEQUENCE: 32
aagccugccu ccaggauguu att                                              23

<210> SEQ ID NO 33
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 33
ttuucggacg gagguccuac aau                                              23

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
gaagctcaga atcagagatt                                                  20

<210> SEQ ID NO 35
<211> LENGTH: 60
<212> TYPE: PRT
<213> ORGANISM: Homo sapiens

<400> SEQUENCE: 35

Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Pro Ser Gly
            20                  25                  30

Pro Gly Gln Pro Ala Pro Ala Ala Thr Gln Ala Ala Pro Gln Ala Pro
        35                  40                  45

Pro Ala Gly His Gln Ile Val His Val Arg Gly Asp
    50                  55                  60

<210> SEQ ID NO 36
<211> LENGTH: 43
<212> TYPE: PRT
<213> ORGANISM: Artificial Sequence
<220> FEATURE:
<223> OTHER INFORMATION: Synthetic peptide

<400> SEQUENCE: 36

Met Asp Pro Gly Gln Gln Pro Pro Gln Pro Ala Pro Gln Gly Gln
1               5                   10                  15

Gly Gln Pro Pro Ala Ala Thr Gln Ala Ala Pro Gln Ala Pro Pro
            20                  25                  30

Ala Gly His Gln Ile Val His Val Arg Gly Asp
        35                  40

<210> SEQ ID NO 37
<211> LENGTH: 43
<212> TYPE: PRT
<213> ORGANISM: Artificial Sequence
<220> FEATURE:
<223> OTHER INFORMATION: Synthetic peptide

<400> SEQUENCE: 37

Met Asp Pro Gly Gln Gln Pro Pro Gln Pro Ala Pro Gln Gly Gln
```

```
                1               5                   10                  15
Gly Gln Pro Pro Ser Ala Ala Thr Gln Ala Ala Pro Gln Ala Pro Pro
                        20                  25                  30

Ala Gly His Gln Ile Val His Val Arg Gly Asp
            35                  40
```

<210> SEQ ID NO 38
<211> LENGTH: 34
<212> TYPE: PRT
<213> ORGANISM: Artificial Sequence
<220> FEATURE:
<223> OTHER INFORMATION: Synthetic peptide

<400> SEQUENCE: 38

```
Met Asp Pro Gly Gln Gln Pro Pro Gln Pro Ala Pro Gln Gly Gln
1               5                   10                  15

Gly Gln Pro Gln Ala Pro Pro Ala Gly His Gln Ile Val His Val Arg
                20                  25                  30

Gly Asp
```

<210> SEQ ID NO 39
<211> LENGTH: 43
<212> TYPE: PRT
<213> ORGANISM: Artificial Sequence
<220> FEATURE:
<223> OTHER INFORMATION: Synthetic peptide

<400> SEQUENCE: 39

```
Met Asp Pro Gly Gln Gln Pro Pro Pro Gln Pro Ala Pro Gln Gly Gln
1               5                   10                  15

Gly Gln Pro Pro Ser Ala Ala Thr Gln Ala Ala Pro Gln Ala Pro Pro
                20                  25                  30

Ala Gly His Gln Ile Val His Val Arg Gly Asp
            35                  40
```

<210> SEQ ID NO 40
<211> LENGTH: 21
<212> TYPE: PRT
<213> ORGANISM: Artificial Sequence
<220> FEATURE:
<223> OTHER INFORMATION: Synthetic peptide

<400> SEQUENCE: 40

```
Met Asp Pro Gly Gln Gln Pro Pro Gln Pro Ala Pro Gln Gly Gln
1               5                   10                  15

Gly Gln Pro Pro Thr
            20
```

<210> SEQ ID NO 41
<211> LENGTH: 20
<212> TYPE: PRT
<213> ORGANISM: Artificial Sequence
<220> FEATURE:
<223> OTHER INFORMATION: Synthetic peptide

<400> SEQUENCE: 41

```
Ala Arg Asn Asp Cys Glu Gln Gly His Ile Leu Lys Met Phe Pro Ser
1               5                   10                  15

Thr Trp Tyr Val
            20
```

METHOD OF USING PRD, PRD-S TAD, ZF7 PEPTIDE OR MIXTURE THEREOF TO INHIBIT CELLULAR RESPONSE TO INFLAMMATORY STIMULI OR TREAT CYTOKINE-STORM-MEDIATED DISEASES

STATEMENT REGARDING ELECTRONIC FILING OF A SEQUENCE LISTING

A Sequence Listing in xml format, submitted under 37 C.F.R. § 1.821, entitled 2022-09-22_Seq_Listing, 9,994 bytes in size, generated on Sep. 21, 2022, and filed via EFS-Web, is provided in lieu of a paper copy. This Sequence Listing is hereby incorporated herein by reference into the specification for its disclosures.

CROSS-REFERENCE TO RELATED APPLICATION

This application claims the priority benefit of China application serial no. 202011323140.4, filed on Nov. 23, 2020. The entirety of the above-mentioned patent application is hereby incorporated by reference herein and made a part of this specification.

BACKGROUND

Technical Field

The present invention relates to the field of biological medicine, in particular to anti-inflammatory peptides (PRD, PRD-S, TAD, and ZF7) that inhibit the cellular response to TNFα, IL-1β, and LPS.

Description of Related Art

Human cells respond to microbial infection by transcribing a number of genes, called effectors, to clear microbes. Some of these gene products, especially cytokines and chemokines, are vital for fending off microbes. For example, LPS from Gram-negative bacteria is the most powerful stimulus to induce expression of these genes. Among the cytokines induced by microbial stimuli such as LPS, TNFα and IL-1β are also strong inducers of cytokines and chemokines, thereby amplifying the inflammatory responses. However, over-production of some of these genes (hyper-inflammation) can cause a serious damage to the body. Sepsis is a potentially life-threatening condition, claiming about 220,000 American lives each year and has a mortality rate estimated 25-50%). Sepsis is caused by the body's extreme response to an infection, producing excessive amounts of cytokines such as IL-1β, IL-6, IL-8, IL-10, IL-18 and TNFα, thus called "cytokine storm". Cytokine storm, however, is not limited to bacterial infections. Cytokine storm in COVID-19, a coronavirus infection, is associated with increased mortality. It can also accompany immunotherapy that activates T cells to fight cancer, known as cytokine release syndrome. Furthermore, in chronic inflammatory or autoimmune diseases such as rheumatoid arthritis (RA) and inflammatory bowel disease (IBD), these cytokines are produced persistently. TNFα is most important since it is mostly responsible for inducing other cytokines and chemokines and thus TNFα inhibitors successfully treat many autoimmune and chronic inflammatory diseases. However, over 40% of patients do not respond to TNF antagonists and some responders develop resistance to the therapy. Therefore, it is necessary to discover new drugs that inhibit the responses to the major inflammatory stimuli (LPS, TNFα, and IL-1β) to treat the diseases where excessive and/or persistent expression of cytokines and chemokines is the underlying problem.

SUMMARY

Excessive and/or persistent production of cytokines and chemokines during acute (e.g. infection) and chronic inflammation (e.g. autoimmune diseases), or in other diseases is a significant clinical problem. The most potent stimuli that induce cytokines and chemokines are TNFα (tumor necrosis factor α), IL-1β (interleukin 1β), and LPS (lipopolysaccharide). In view of the above-mentioned technical problems, the present invention has discovered 4 peptides, named PRD, PRD-S, TAD, and ZF7 that inhibit the response to these stimuli in different cell types including fibroblasts, monocytes and epithelial cells, also in vivo. Their sequences are as follows.

```
PRD peptide sequence:
                                    (SEQ ID NO: 1)
GQPPSQPPQGQGPPSGPGQPAPAATQAAPQ

PRD-S:
                                    (SEQ ID NO: 2)
QPPGQGPPSGPGQPA

TAD sequence:
                                    (SEQ ID NO: 3)
RQAMRININPSTANSPKCQE ZF7 sequence:
                                    (SEQ ID NO: 4)
PPKQRCRAPACDHFGNAKCNGYCNECYQFKQMYG
```

The object of the present invention is achieved by the following technical aspects:

In one aspect, the present invention provides a method of using PRD, PRD-S,TAD, ZF7 peptide or a mixture thereof to inhibit the cellular response to inflammatory stimuli, wherein the amino acid sequence of the PRD peptide is SEQ ID NO: 1, the amino acid sequence of the PRD-S peptide is SEQ ID NO: 2, the amino acid sequence of the TAD peptide is SEQ ID NO: 3, and the amino acid sequence of the ZF7 peptide is SEQ ID NO: 4.

The research concept of the present invention is as follows: Relevant studies show that YAP1 (Yes-associated protein 1) is a transcription factor which activates transcription of genes related to cell proliferation and apoptosis inhibition. At present, the research on YAP1 mainly focused on YAP1 as a transcription factor, and YAP1 had been found to have an inhibiting effect on the signal pathway of the tumor necrosis factor TNF-α, but the specific inhibiting mechanism is not clear thus far. The present invention has revealed on the basis of the existing research that: in human Fibroblast-Like Synoviocytes (FLS) cells, YAP1 also inhibits TNF-α induced gene expression. Through YAP1 knockdown experiments, it has been found that: TNF-α induced gene expression is up-regulated when YAP1 protein expression is suppressed; similar phenomena are found in other cell lines such as HCT-8 cells of human colonic epithelial cells, THP-1 cells of human monocytic cells and human Peripheral Blood Mononuclear Cells (PBMCs). Furthermore, the present invention finds through YAP1 knockout experiments that the experimental results obtained by YAP1 knockout and YAP1 knockdown are similar, and the expression level of YAP1 protein in YAP1 knockout cells is not obviously different from that in non-knockout cells. In subsequent experiments, through cloning and analysis of YAP1 messenger RNAs, it is found that the knockout cells express various mutant YAP1 proteins with in-frame deletions of the PRD peptide segment, which is the key region for inhibiting response to inflammatory stimulations in YAP1 protein. Furthermore, on the basis of finding the PRD peptide, and by overexpressing and analyzing the structures and functions of different isoforms of YAP1 protein, the present invention finds that a Trans-Activation Domain (TAD peptide segment) on YAP1 protein can also inhibit the signal pathway of TNF-α, IL-1β and LPS.

Although YAP1 has been extensively studied and the main role thereof has been defined as inhibiting signals of the tumor necrosis factor TNF, the specific mechanism for YAP1 to inhibit signals of TNF is still not fully understood, and the reported possible mechanisms are also completely different from those found in the research of the present invention. Previously, YAP1 was primarily known as a co-transcription factor, especially in an inflammatory signaling pathway, but the role of YAP1 other than a transcription factor has not been revealed. Functions of different isoforms (subtypes) of YAP1 has long been thought to be the same, whereas the present invention reveals for the first time that one YAP1 isoform (YAP9) acts as a non-transcription factor to inhibit the inflammatory signal pathway, and another YAP1 isoform (YAP2) performs a completely opposite function due to the presence or/and absence of different peptides in the protein, showing that the inhibitory effect of YAP1 is realized by two critical peptides within the protein, PRD and TAD. Therefore, synthetic PRD and TAD peptides can mimic the anti-inflammatory function of YAP1, which inhibits the response to inflammatory stimuli.

Next, the present invention investigated how YAP9 inhibits the cellular response to TNFα, IL-1-β, and LPS. Although these 3 stimuli share the distal signaling molecules such as NF-κB and MAP kinases, they use different signaling molecules proximal to each receptor. Therefore, we hypothesized that YAP9 must be regulating a negative signaling molecule shared by all 3 stimuli. One of the candidates is A20 also known as TNFAIP3 (TNFα-induced protein 3) that inhibits the signaling transduction by all 3 stimuli. Therefore, we tested whether YAP9 (or YAP2) physically associates with A20. The results showed that both YAP2 and YAP9 pulled down A20 but YAP9 had a higher affinity to A20 than YAP2 since YAP9 pulled down much more A20 than YAP2 did although the YAP2 expression level was much higher than YAP9.

Next, we investigated whether the interaction between YAP9 and A20 is necessary for them to suppress the inflammatory responses. Indeed, A20 over-expression (OE) no longer suppressed the TNFα response when YAP1 (all isoforms) was depleted, and similarly YAP9 OE no longer suppressed the TNFα response when A20 was depleted. Because YAP9 contains full-length PRD and TAD peptide and PRD and/or TAD peptide play an inflammatory inhibitory role, in some embodiments, when using PRD peptide, TAD peptide or a mixture thereof to inhibit the cellular response to inflammatory stimulations, A20 protein (or ZF7 peptide) can be added so that A20 protein can work with PRD peptide and TAD peptide in concert.

Recent findings identified the ZF7 (zinc finger domain 7) as the key domain for A20 to suppress inflammation. We hypothesized that ZF7 peptide inhibit the TNFα response just as PRD and TAD peptides do, and indeed it inhibited the inflammatory response in vitro. Next, we tested whether ZF7 inhibits LPS response in vivo. We injected mice with a high dose of LPS (200 µg/mouse) or LPS+ZF7 (200 µg/mouse) and collected the sera after 3 hours. ZF7 almost completely inhibited all the cytokines and chemokines measured.

Next, we investigated how PRD, TAD, and ZF7 peptides inhibit the TNFα response. The PRD, TAD, and ZF7 peptide have the same effect as either YAP9 OE (over-expression) or A20 OE, respectively. As YAP9 OE or A20 OE is futile in the absence of the other, PRD or TAD peptide also requires the presence of A20 while ZF7 peptide the presence of YAP9. Our data provide the mechanism by which the YAP9-A20 complex suppresses the TNFα response.

In some embodiments, cells are selected from the group consisting of fibroblasts (such as FLS), monocytes (such as THP-1) and epithelial cells (such as HCT-8).

In some embodiments, inflammatory stimuli are selected from the group consisting of TNF-α, IL-1β and LPS.

In some embodiments, the PRD, PRD-S, TAD, ZF7 peptide, or a mixture thereof can inhibit gene expression induced by the inflammatory stimuli.

In some embodiments, wherein the inflammatory genes are selected from the group consisting of IL-6, IL-8, CXCL10, IL-32, CCL2, CCL20 and COX-2.

TNF-α stimulation, IL-1β stimulation or LPS stimulation can also induce the production of other cytokines and chemokines in the body, and transitional activation of the cytokines and the chemokines will lead to "cytokine storms" which can damage the body. As the present invention can inhibit gene expression induced by the inflammatory stimuli, it can be used for treating cytokine-storm-mediated diseases.

In another aspect, the present invention has provided a method of using PRD, PRD-S, TAD, ZF7 peptide or a mixture thereof to treat cytokine-storm-mediated diseases, wherein the amino acid sequence of the PRD peptide is SEQ ID NO: 1, the amino acid sequence of the PRD-S peptide is SEQ ID NO: 2, the amino acid sequence of the TAD peptide is SEQ ID NO: 3, and the amino acid sequence of the ZF7 peptide is SEQ ID NO: 4.

In some embodiments, cytokine-storm-mediated diseases are selected from the group consisting of autoimmune diseases, bacterial or viral infections, and cytokine release syndromes caused by tumor immunotherapy.

In some embodiments, the diseases are selected from the group consisting of septicemia, COVID-19, inflammatory bowel diseases, rheumatoid arthritis and sepsis.

DESCRIPTION OF THE EMBODIMENTS

Figure 1A:
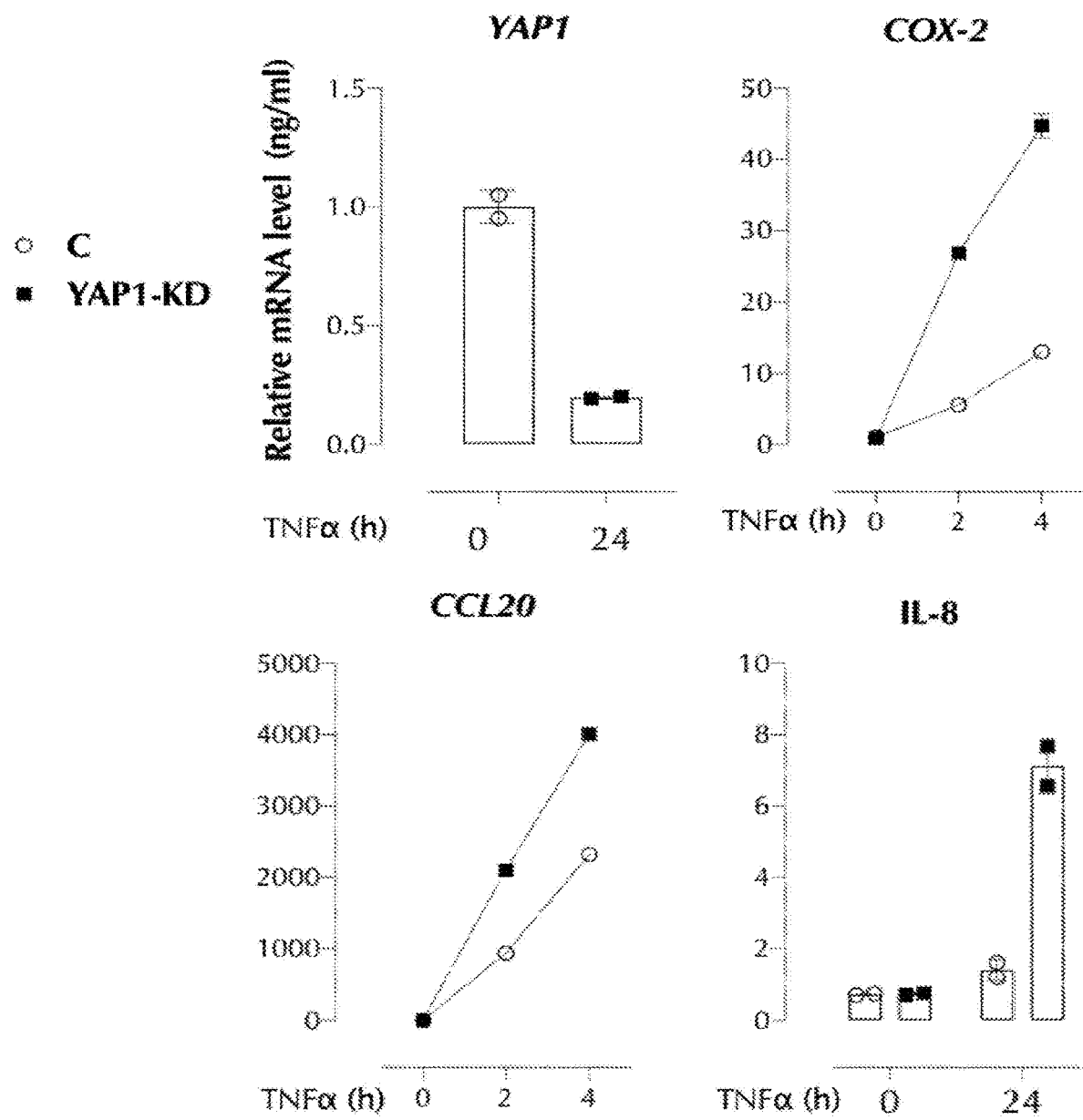
FIG. 1A shows that YAP1 knockdown (KD) enhances the expression of TNFα-induced genes in FLS. FLS were transfected with control (C) or YAP1 siRNA as described in the method and stimulated with TNFα (1 ng/ml) for the indicated time periods. The mRNA expression was measure by qPCR and the IL-8 protein level by ELISA. The statistical significance was calculated by unpaired Student t test (*: $p<0.05$, : $p<0.01$, *: $p<0.001$, ***: $p<0.0001$). The results are the representative of 5 similar experiments.

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination.

Inhibit or inhibiting: The term "inhibit" or "inhibiting" as used herein refers to prohibit or prohibiting from doing something such as proliferation.

Treatment or treating: The term "treatment" or "treating" as used herein refers to therapeutic treatment wherein the object is to slow down (lessen) if not cure the targeted pathologic condition or disorder or prevent recurrence of the condition.

Induce, induction or inducing: The term "induce", "induction" or "inducing" as used herein refers to cause, or causing.

Throughout, various aspects of the invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 5 should be considered to have specifically disclosed sub-ranges such as from 1 to 3, from 1 to 4, from 2 to 4, from 3 to 5 etc., as well as individual numbers within that range, for example, 1, 2, 3, 4, and 5. This applies regardless of the breadth of the range.

Other objects, advantages and features of the present invention will become apparent from the following specification taken in conjunction with the accompanying drawings.

In order to show a clear understanding of the technical features, purposes and effects of the present invention, the specific embodiments of the present invention will now be described in detail with reference to the drawings. Obviously, the described embodiments are only a part of the embodiments of the present invention, but not all the embodiments. Based on the embodiments of the present invention, all other embodiments obtained by those of ordinary skill in the art without creative work will fall within the protection of the present invention.

Materials and Methods

Reagents

RPMI, DMEM, and other cell culture media are from Gibco; fetal bovine serum from Biological Industries; RNAiMAX and Pierce Protein Transfection Reagent from ThermoFisher; all the antibodies used in this study were purchased from Cell Signaling Technology. Recombinant human IL-1β and TNFα were purchased from Peptrotech, and LPS from Sigma. All peptides were synthesized by GenScript.

Cell Culture

Human PBMCs and THP-1 cells were cultured in RPMI-1640 while FLS and HCT-8 cells in DMEM, supplemented with 10% fetal bovine serum and maintained in a humidified incubator at 37° C. with 5% CO2 in air.

IL-8 ELISA

IL-8 LEISA kit was purchased from ThermoFisher and ELISA was performed according to the manufacturer's instruction.

FACS Analysis

To measure YAP1 expression by flow cytometry in PBMCs, cells were fixed and permeabilized using CytoFix/CytoPerm buffers (BD Biosciences) according to the manufacturer's instruction. Cells were stained with anti-YAP1 antibody-FITC (Cell Signaling Technology) and measured by flow cytometry (FACSVerse, BD Biosciences). Human PBMCs were stained with anti-CD14 antibody-PE and anti-CD3 antibody-APC before being fixed and permeabilized.

Human PBMCs Isolation

The study was approved by the institutional ethics committee of School of Basic Medical Sciences of Guangzhou Medical University and a signed informed consent was obtained from every participant before being included into the study. Blood was drawn into heparin sodium-containing tubes (K2E Vacutainer, BD) from healthy volunteers (age: 25-45) in the laboratory (non-shipped). Samples were processed within 2 hours. The time interval between the two blood drawings of each individual was 20-30 days and none of the individuals showed or reported any disease symptoms.

All steps of PBMC preparation were carried out at room temperature. The blood from the same donor was pooled and mixed 1:1 with pre-warmed (room temperature) 1×PBS (without $Ca^{2+}$ or $Mg^{2+}$). The mixture was layered onto Lymphoprep (Stem Cell Technologies) in a SepMate™ tube and centrifuged at 1200rcf for 10 min. The top layer containing enriched mononuclear cells was poured into a new tube and washed with PBS containing 2% FBS twice by centrifuging at 300rcf for 8 min.

Western Blotting (WB) and Immunoprecipitation (IP)

All antibodies used in WB were purchased from Cell Signaling Technology. IP was performed by adding the indicated antibody and protein A-beads to the cell lysates.

Nucleic Acid Extraction and RNA Reverse Transcription

Total RNA was extracted from cells, using Trizol method according to the manufacturer's protocol (ThermoFisher Scientific). Extracted RNA was dissolved in RNase-free and DNase-treated water and then immediately reverse-transcribed using HiScript Q RT SuperMix for qPCR (Vazyme, China). cDNA was stored at −20° C. for subsequent qPCR analyses.

qPCR qPCR reactions were performed with ChamQ Universal SYBR qPCR Master Mix (Vazyme, Biotech) in LightCycler® 480 Instrument (Roche, Basel, Switzerland).

PCR primers

All genes measured are human.

| Gene | Forward primer | Reverse Primer |
|---|---|---|
| CCL20 | CAACTTTGACTGCTGTCTTGG ATA (SEQ ID NO:5) | TTGACTTTTTTACTGAGGAGA CGC (SEQ ID NO:6) |
| IL-8 | CTTGGCAGCCTTCCTGATTT (SEQ ID NO:7) | TTCCTTGGGGTCCAGACAGA (SEQ ID NO:8) |
| GAPDH | ATCACCATCTTCCAGGAGCGA G (SEQ ID NO:9) | GGGCAGAGATGATGACCCTTT TG (SEQ ID NO:10) |
| CXCL10 | GTGGCATTCAAGGAGTACCTC (SEQ ID NO:11) | TGATGGCCTTCGATTCTGGAT T (SEQ ID NO:12) |
| IL6 | ACTCACCTCTTCAGAACGAAT TG (SEQ ID NO:13) | CCATCTTTGGAAGGTTCAGGT TG (SEQ ID NO:14) |
| CCL3 | CGGCAGATTCCACAGAATTTC (SEQ ID NO:15) | AGGTCGCTGACATATTTCTGG (SEQ ID NO:16) |
| COX-2 | TAAGTGCGATTGTACCCGGAC (SEQ ID NO:17) | TTTGTAGCCATAGTCAGCATT GT (SEQ ID NO:18) |
| CCL2 | GCAATCAATGCCCCAGTCAC (SEQ ID NO:19) | TGCTTGTCCAGGTGGTCCAT (SEQ ID NO:20) |
| IL-32 | GAAGGTCCTCTCTGATGACA (SEQ ID NO:21) | AAGTAGAGGAGTGAGCTCTG (SEQ ID NO:22) |
| YAP1 | CCCTCGTTTTGCCATGAAC (SEQ ID NO:23) | GTTGCTGCTGGTTGGAGTTG (SEQ ID NO:24) |
| A20 | GCCTCCAGGATGTTACCAGG (SEQ ID NO:25) | GGCCTCTGCTGTAGTCCTTT (SEQ ID NO:26) |

YAP1 siRNA

```
                                              (SEQ ID NO:27)
Sense:
5'-GACAUCUUCUGGUCAGAGATT-3'

(SEQ ID NO:28)
Antisense:
5'-UCUCUGACCAGAAGAUGUC-3'.
```

YAP1 KO construct

For CRISPR/Cas9 knockout of human YAP1, the following two small guide RNAs (sgRNAs) were used to delete a region within the proline-rich domain (PRD):

```
                                              (SEQ ID NO:29)
sgRNA#1 :
CCCTGCGGGGGCTGCGAAGG (SEQ ID NO:30)
sgRNA#2:
ACCCGGGCAACCGGCACCCG.
```

Both gRNA sequences were cloned into the vector pGE-4 (pU6gRNA1U6gRNA2Cas9puro). Cells were transfected with indicated plasmid followed by extensive selection with 2 μg/ml puromycin.

YAP1 KD Lentiviruses production and uses

```
                                              (SEQ ID NO:31)
YAP1 shRNA:
AAAAGACATCTTCTGGTCAGAGATTGGATCCAATCTCTGACCAGAAGAT
GTC.
```

The above YAP1 shRNA was cloned into the lentiviral vector LV5 and lentiviruses were produced as described. Target cells were infected with the viruses with polybrene (5 μg/ml). Cells were selected using puromycin (5 μg/ml).

A20 siRNA

```
                                              (SEQ ID NO:32)
Sense:
5'-AAGCCUGCCUCCAGGAUGUUATT-3'

(SEQ ID NO:33)
Antisense:
5'-TTUUCGGACGGAGGUCCUACAAU-3'.
```

A20 KO Construct

For CRISPR/Cas9 knockout of human A20, the following sgRNA was used to create a KO construct in LV5.

```
                                              (SEQ ID NO:34)
sgRNA:
GAAGCTCAGAATCAGAGATT.
``` siRNA Transfection with RNAiMAX

Cells are transfected using Lipofectamine RNAiMAX (Life Technologies, Grand Island, N.Y.). The day prior to transfections, cells are plated on cell-culture plates (Corning) at 500 μL/well for 12-well plates and 1 ml/well for 6-well plates at density of $4 \times 10^5 - 5 \times 10^5$ cells/mL in the indicated growth medium and propagated to 80% confluency at the time of transfection. Transfection was performed according to the manufacturer's instruction.

Legendplex™

To simultaneously quantify the concentration of the soluble inflammatory cytokines and chemokines, the cell culture supernatant was analyzed by using the bead-based multiplex LEGENDplex™ (Biolegend) according to the manufacturer's instruction.

Electroporation of THP-1 siRNAs or plasmids were introduced into cells by Neon Transfection System (Invitrogen) according to the manufacturer's protocol. After the cells were pre-incubated in complete cell culture medium containing the nucleic acid transfection enhancer NATE (1%) for 30 min, the electroporation pipette tip was filled with $2 \times 10^6$ cells in transfection R buffer containing siRNA/plasmids. Three milliliters of Electrolytic buffer were added to a buffer container. The electrical conditions were set at 1,600V, 10 ms, and 3 pulses. After electroporation, cells were rapidly dispensed into 5 ml round bottom sterile tubes using a pipette, and were then cultured in a CO2 incubator at 37° C.

Peptide Transfection

Peptides were transfected into the cells using Pierce Protein Transfection Reagent Kit™ according to the manufacturer's instruction. The Pierce Reagent in methanol was pipetted into a tube and the solvent was evaporated in the hood. Peptides were diluted in PBS and mixed with the dried Pierce Reagent. The peptides/Reagent complex was added to the cells in serum-free medium. After 4 hours, the medium containing serum was added to the cells and the cells were used for experiments.

1. YAP1 Suppresses the TNFα Response

YAP1 (Yes-associated protein-1) is a transcriptional regulator that activates the genes involved in cell proliferation and suppressing apoptotic genes. We found that it also suppresses expression of TNFα-induced genes in human FLS (Fibroblasts-Like Synoviocytes). FLS were transfected with control or YAP1-targeting siRNA using Lipofectamine RNAiMAX™ according to the manufacturer's instruction. After 2 days, the cells were treated without or with TNFα (1 ng/ml) as indicated, and the IL-8 protein level and the mRNA levels of COX-2 and CCL20 were measured by and ELISA and qPCR, respectively. The data show that expression of TNFα-induced genes is significantly elevated when YAP1 is depleted (FIG. 1A), indicating that YAP1 suppresses induction of these genes.

Figure 1B:
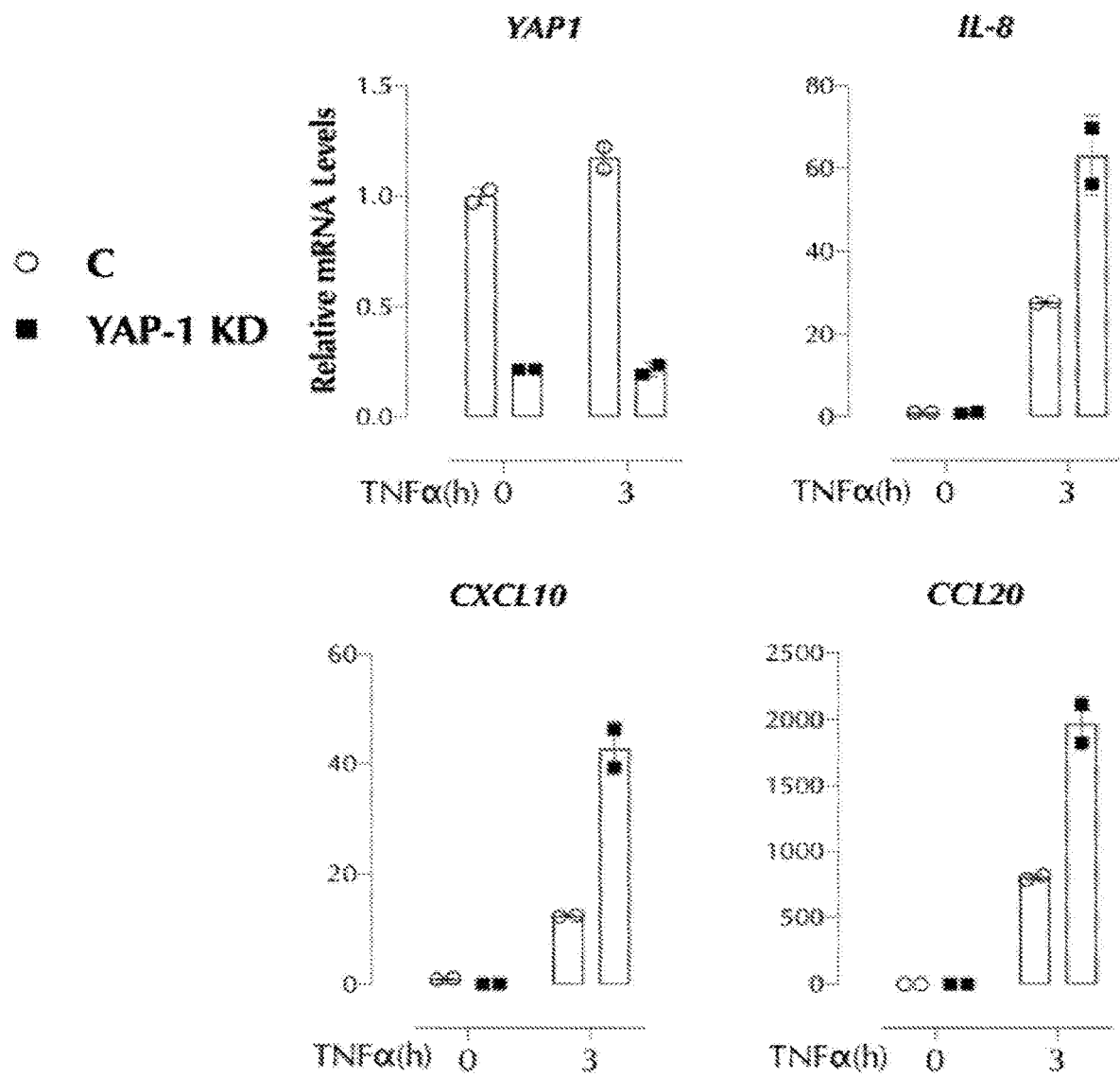
FIG. 1B shows that YAP1 knockdown (KD) enhances the expression of TNFα-induced genes in HCT-8. HCT-8 cells were transfected with control (Ctrl) or YAP1 siRNA and stimulated with TNFα (2 ng/ml) for 3 h. The mRNA expression was measure by qPCR. The statistical significance was calculated by unpaired Student t test (*: $p<0.05$, : $p<0.01$, *: $p<0.001$, ***: $p<0.0001$). The results are the representative of 5 similar experiments.
Figure 1C:
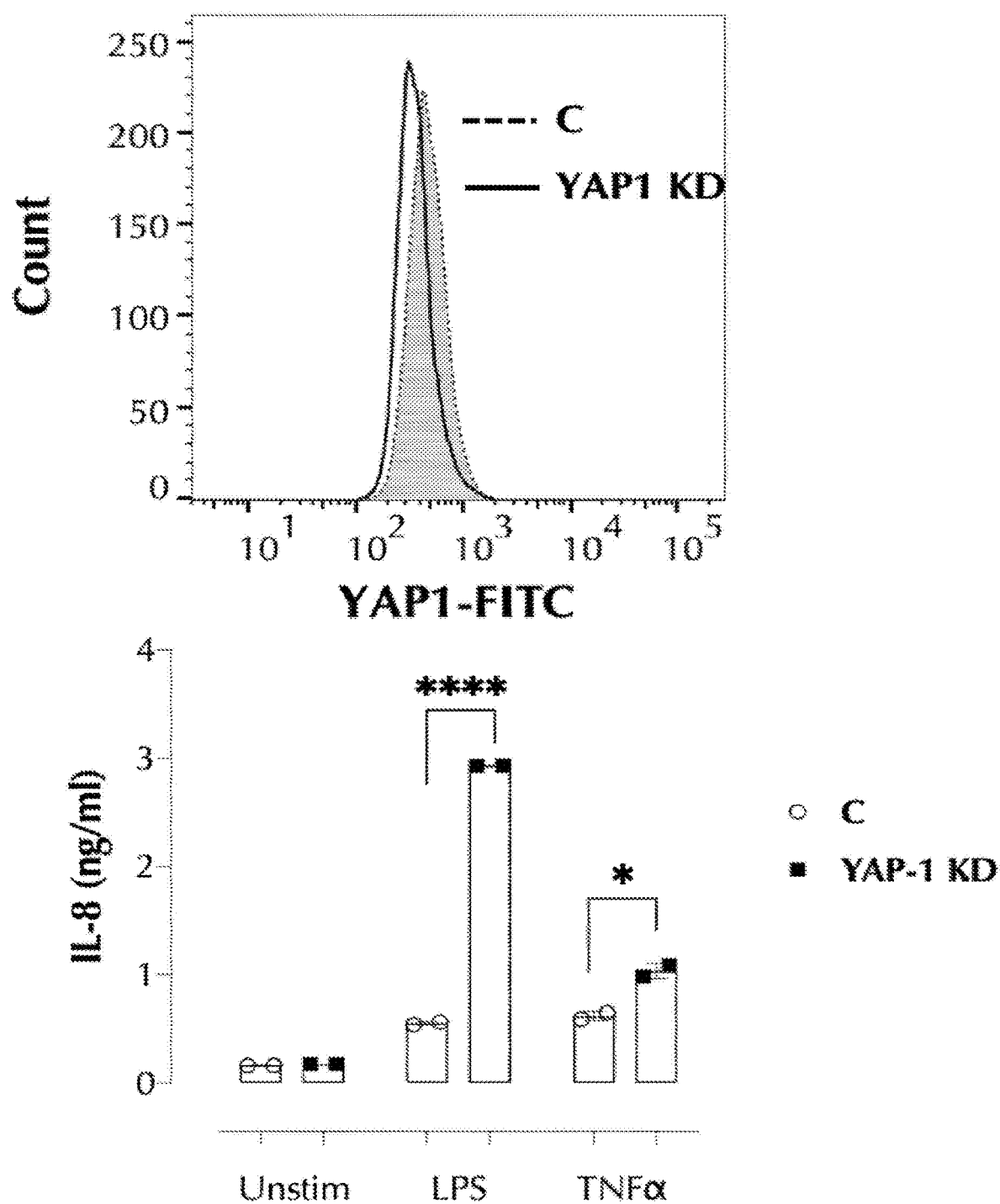
FIG. 1C shows that YAP1 knockdown (KD) enhances the expression of TNFα-induced IL-8 in THP-1. THP-1 cells were transfected with control (C) or YAP1 siRNA by electroporation and stimulated with TNFα (5 ng/ml) or LPS (200 ng/ml) for 24 hours. YAP-1 expression level was measured by flow cytometry and IL-8 protein level in the medium was measured by ELISA. The statistical significance was calculated by unpaired Student t test (*: $p<0.05$, : $p<0.01$, *: $p<0.001$, ***: $p<0.0001$). The results are the representative of 2 similar experiments.
Figure 1D:
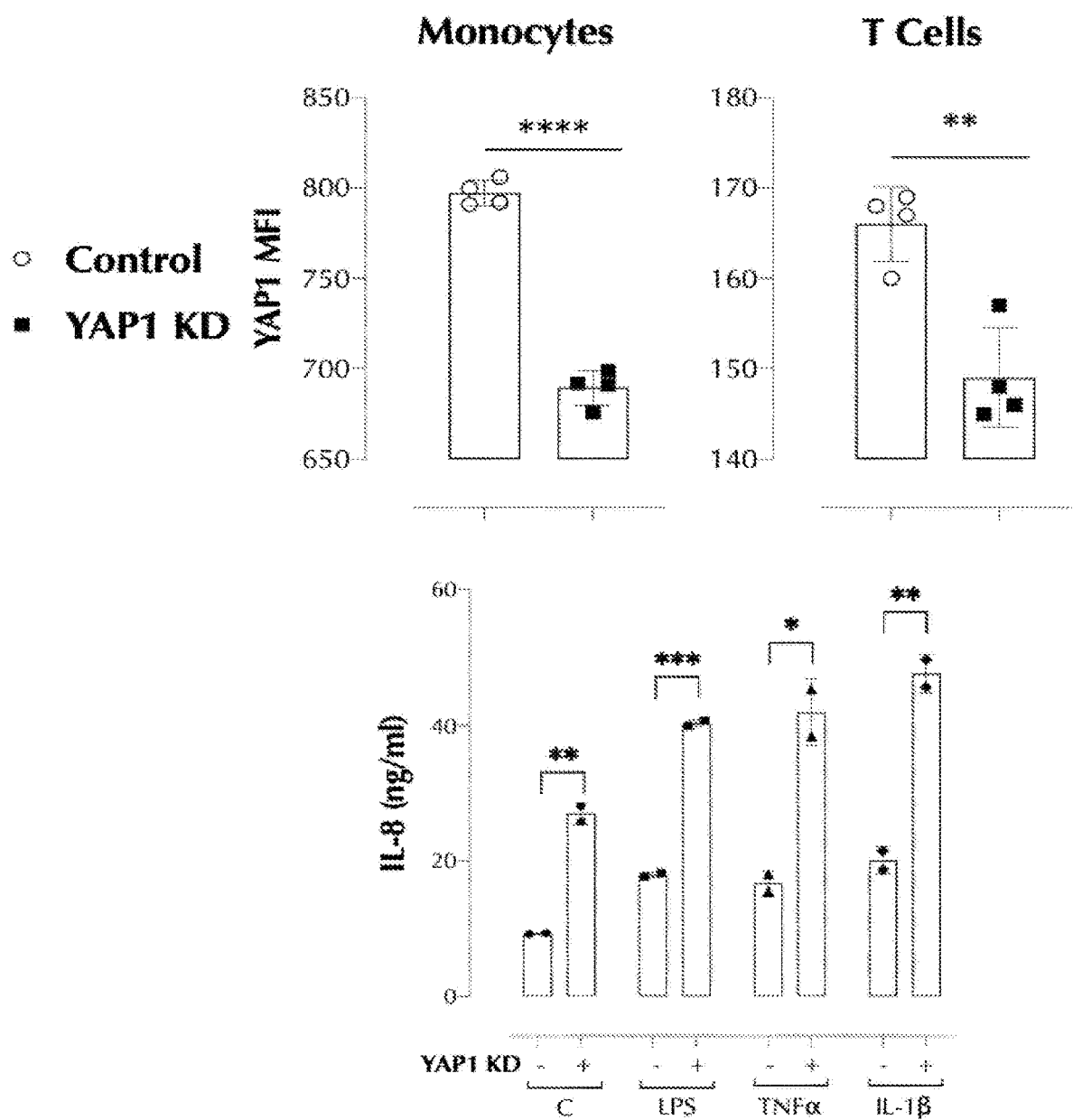
FIG. 1D shows that YAP1 knockdown (KD) enhances the expression of TNFα-induced IL-8 in human PBMCs. PBMCs were transfected with control or YAP1 shRNA by lentiviruses as described in the method and stimulated with TNFα (2 ng/ml), IL-1β (2 ng/ml), or LPS (50 ng/ml) for 24 hours. YAP-1 expression level was measured by flow cytometry and IL-8 protein level in the medium was measured by ELISA. Monocytes were stained with anti-human CD14 antibody and T cells with anti-human CD3 antibody, respectively. The statistical significance was calculated by unpaired Student t test (*: $p<0.05$, : $p<0.01$, *: $p<0.001$, ***: $p<0.0001$). The results are the representative of 3 similar experiments.

The same effect was reproduced in other cell types including a human epithelial cell line (HCT-8, FIG. 1B), a human monocytic cell line (THP-1, FIG. 1C), and fresh human peripheral blood mononuclear cells (PBMCs, FIG. 1D). HCT-8 cells were transfected using Lipofectamine RNAiMAX™, while THP-1 cells were transfected by electroporation and PBMCs using Lentiviruses expression control or YAP1 shRNA. In all cell types, the reduction of YAP1 expression enhanced the expression of TNFα-induced genes.

Figure 2A:
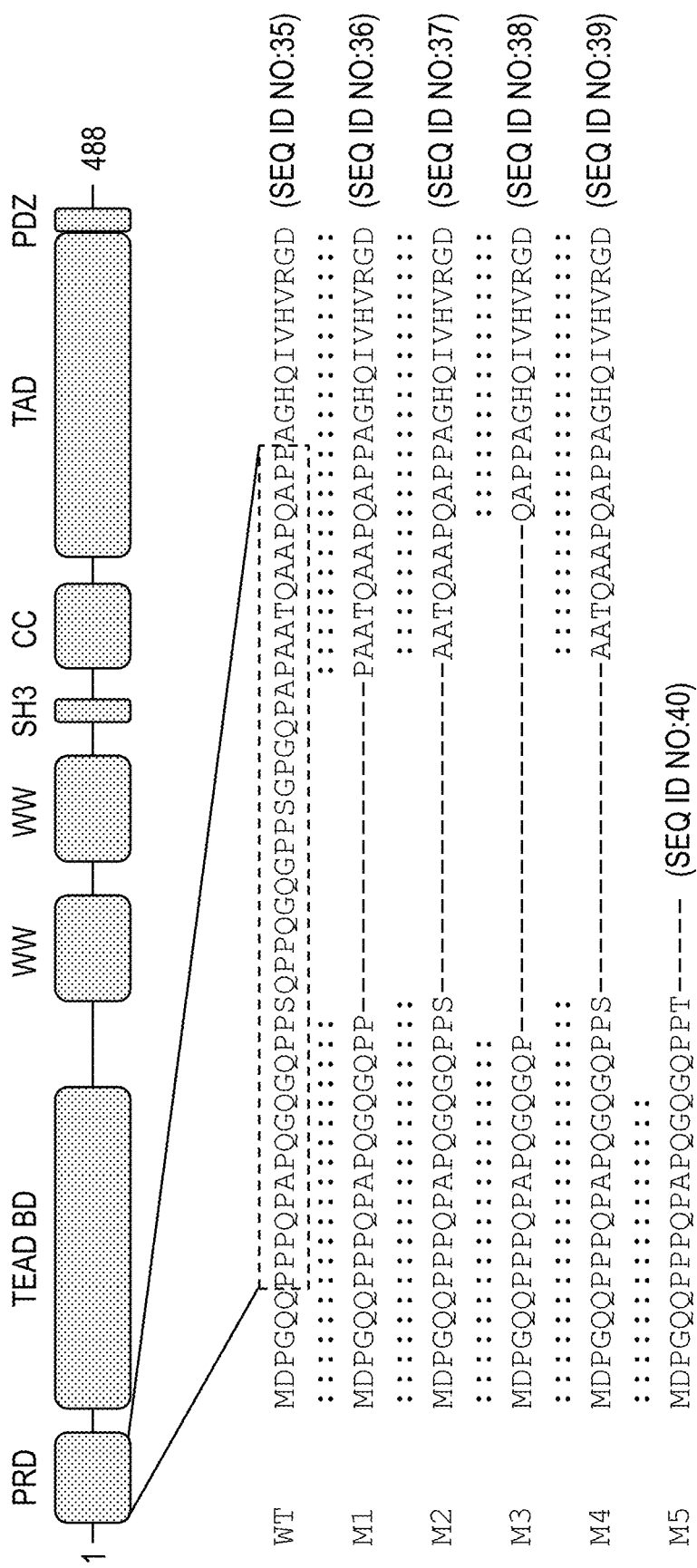
FIG. 2A shows that Proline-rich domain (PRD) is mutated in YAP1 KO mRNA clones. (PRD: proline-rich domain, TEAD BD: TEAD binding domain, WW: tryptophan-tryptophan domain, SH3: SRC Homology 3 Domain, CC: coiled coil domain, TAD: transactivation domain, PDZ: PSD-95, DLG, ZO-1 domain).
Figure 2B:
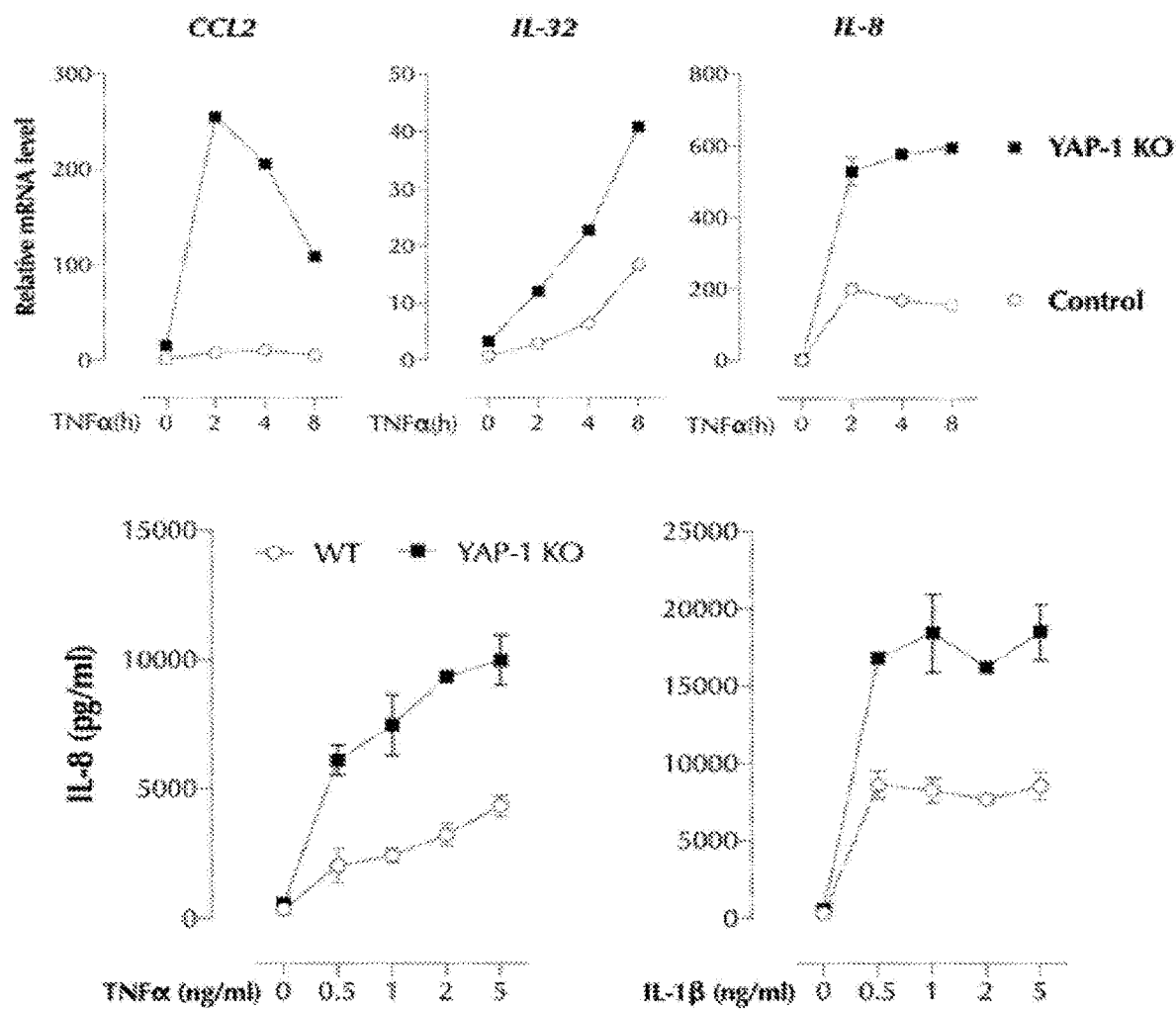
FIG. 2B shows that YAP1 KO in HCT-8 cells enhances the response to TNFα and IL-1β. YAP1 was knocked out in HCT-8 cells as described in the method and stimulated with TNFα (2 ng/ml) for the indicated time periods for mRNA levels and with TNFα (2 ng/ml) or IL-1β (1 ng/ml) 24h for ELISA. The results are the representative of 4 similar experiments.
Figure 2C:
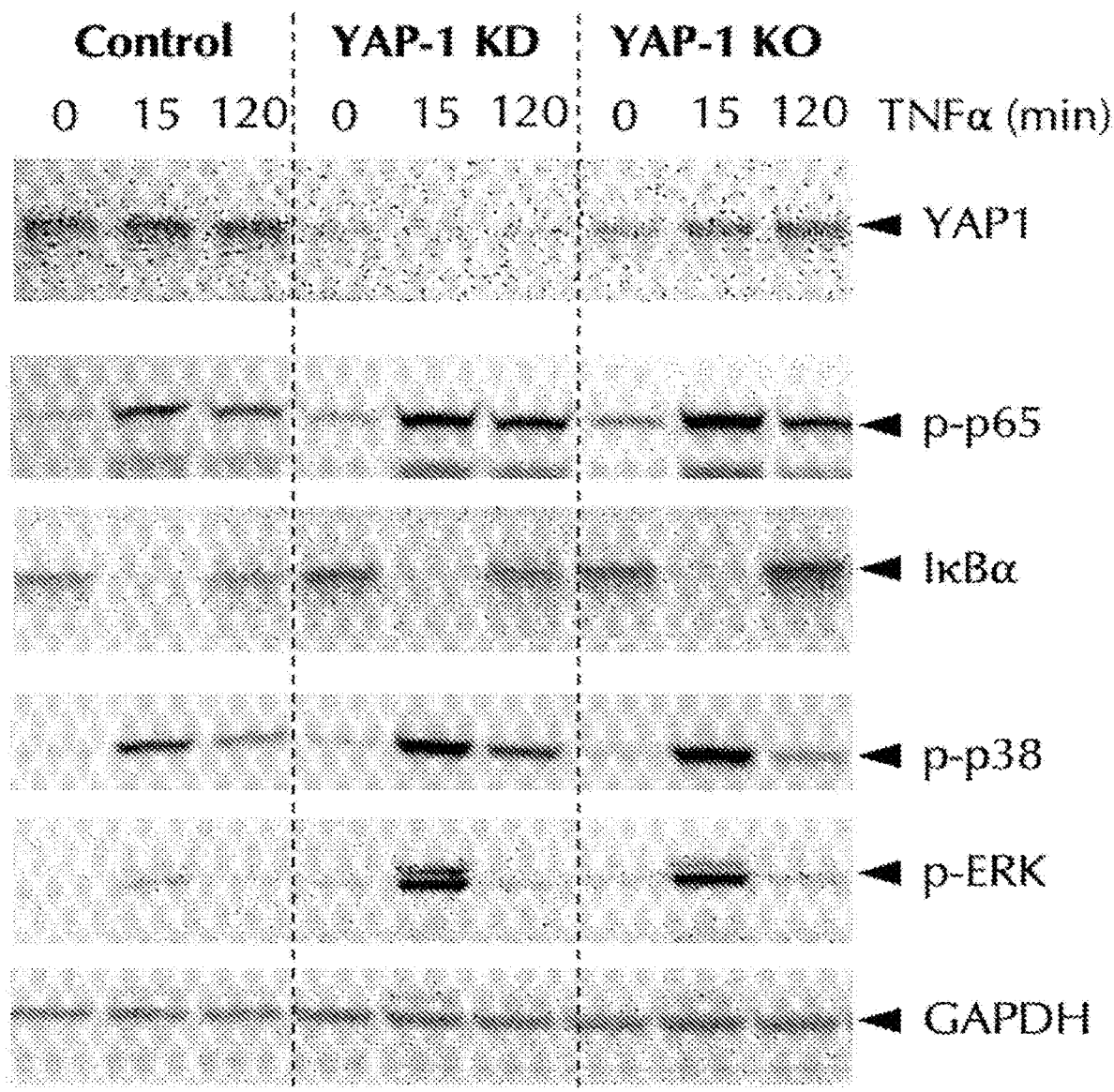
FIG. 2C shows that YAP1 KD or KO enhances the TNFα-induced signaling pathways in HCT-8. Control, YAP1 KD or KO cells were stimulated with TNFα (2 ng/ml) for the indicated time periods. The total cell lysates were subjected to western blotting with the indicated antibodies. The results are the representative of 2 similar experiments.

2. YAP1 KO (Knockout) Reveals PRD within YAP1 Protein as a Negative Regulator of TNFα Signaling To further confirm the findings from YAP1 KD study in a more precise fashion, we performed CRISPR/Cas9-mediated YAP1 KO in HCT-8 cells to delete a region within the proline-rich domain (PRD, seen as FIG. 2A). YAP1 KO produced the same effects as YAP1 KD, enhancing the TNF response. In addition, YAP1 KO also enhanced the response to IL-1β stimulation (FIG. 2B). Next, we investigated whether YAP1 inhibits the TNFα signaling pathways. TNFα rapidly activates multiple pathways, leading to transcription of genes including cytokines and chemokines. Among the pathways, NF-κB and MAP kinases are most important for transcription of inflammatory genes. Either YAP1 knockdown (KD) or knockout (KO) significantly enhanced the activation measured by the phosphorylation (p) levels, of p65 (p-p65, a member of NF-κB), and p38 and ERK (p-38, and p-ERK, the members of the MAP kinase family) (FIG. 2C). Surprisingly, however, the YAP1 protein was still present in YAP-1 KO cells (FIG. 2C). To verify that the gene was modified as intended, we cloned 8 YAP1 mRNAs from the KO cells. The sequencing reveealed that all 8 mRNAs were mutated and that 7 out of 8 YAP1 mRNAs had an in-frame deletion of various sizes in the proline-rich domain (PRD) while one of them (M5) had an out-of-frame deletion resulting in premature termination in translation. All in-frame deletion mutants were translated into truncated YAP-1 protein (FIG. 2A), which explained the presence of YAP1 protein in KO cells. Therefore, we hypothesized that YAP1 uses PRD to suppress the response to inflammatory stimuli since mutations in PRD increased the response.

Figure 3A:
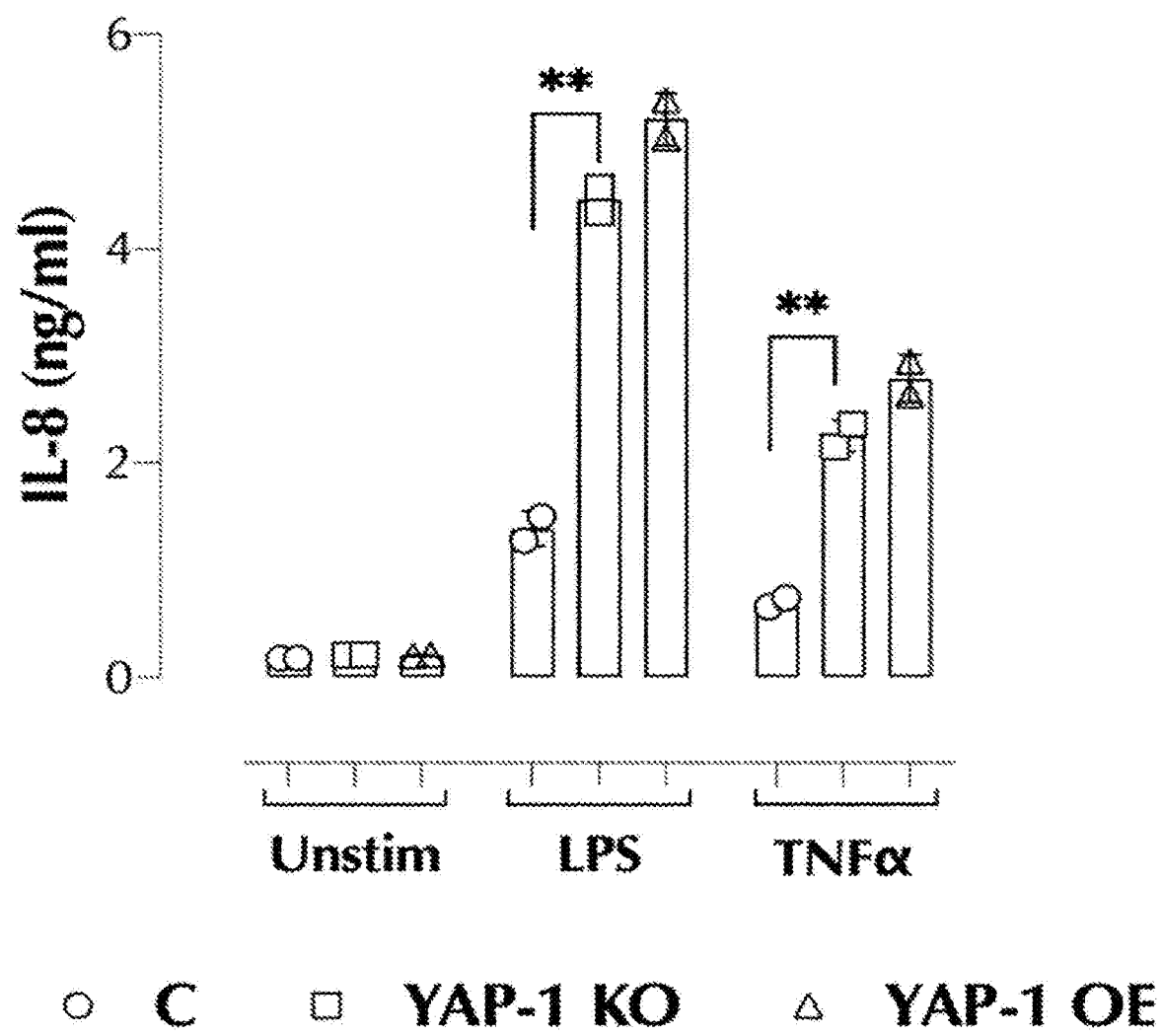
FIG. 3A shows that YAP1 OE or KO in THP-1 cells enhances IL-8 expression induced by TNFα or LPS. THP-1 cells were transfected with C (Control), YAP1 (isoform 2) OE, or KO construct by electroporation and stimulated with LPS (200 ng/ml) or TNFα (5 ng/ml) for 24 hours and IL-8 protein level in the medium was measured by ELISA. The results are the representative of 3 similar experiments.
Figure 3B:
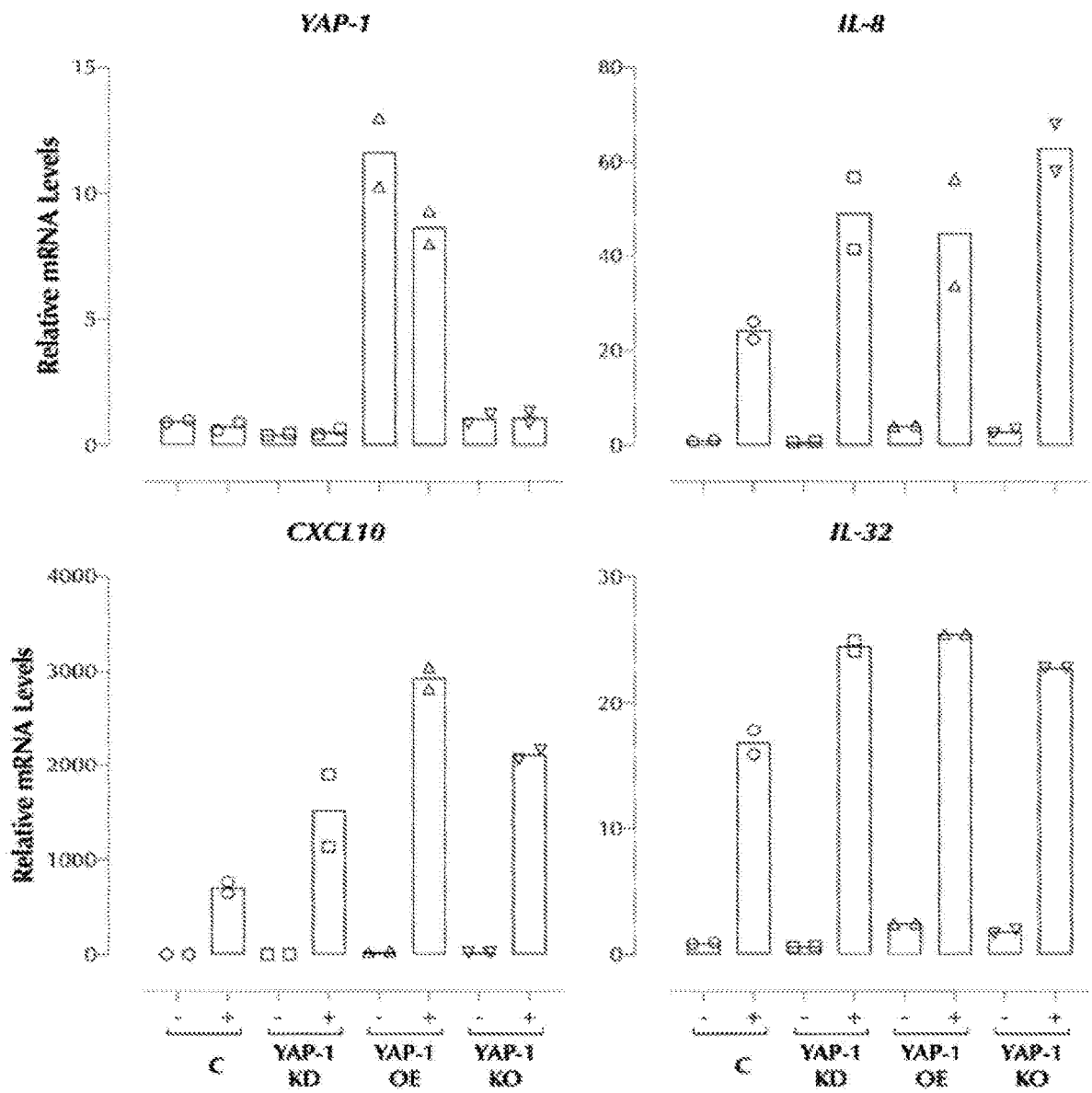
FIG. 3B shows that YAP1 KD, KO, or OE enhances the expression of TNFα-induced genes in HCT-8. YAP1 KD, KO, and OE (isoform 2) HCT-8 cells were prepared as described in the method and stimulated with TNFα (2 ng/ml) for 3 hours. The mRNA levels of the indicated genes were measure by qPCR. The results are the representative of 3 similar experiments.
Figure 3C:
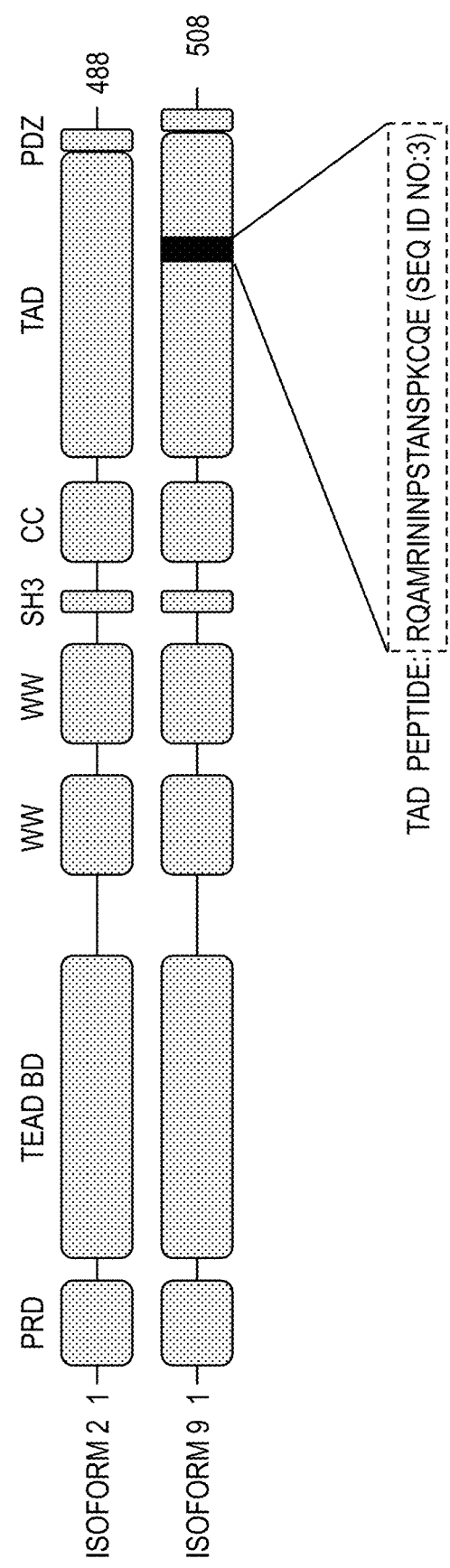
FIG. 3C shows that YAP1 isoform 2 (herein YAP2) lacks a small peptide in TAD (transactivation domain) of YAP1 compared to YAP1 isoform 9 (herein YAP9). When the protein sequences of the two isoforms were aligned, isoform 2 lacked a small stretch of amino acids in TAD. Therefore, we hypothesized YAP1 uses this peptide to suppress the signaling by pro-inflammatory stimuli. When isoform 2 is over-expressed, it may hinder other isoforms with the complete TAD to inhibit the signaling by pro-inflammatory stimuli. (PRD: proline-rich domain, TEAD BD: TEAD binding domain, WW: tryptophan-tryptophan domain, SH3: SRC Homology 3 Domain, CC: coiled coil domain, TAD: transactivation domain, PDZ: PSD-95, DLG, ZO-1 domain).

3. YAP1 OE (Over-Expression) Reveals Another Short Peptide TAD in YAP1 Protein as a Negative Regulator of the Inflammatory Response Since YAP1 depletion (KD) enhances the expression of genes induced by TNFα, IL-1β, or LPS, we hypothesized that YAP1 OE would suppress the response to these stimuli. Contrary to our expectation, YAP1 OE enhanced the expression of genes induced by TNFα or LPS in THP-1 (FIG. 3A) or HCT-8 cells just like YAP1 KD or KO did (FIG. 3B). We then realized that as YAP1 is expressed in at least 8 different isoforms in different cell types, different isoforms may have different functions in the inflammatory response. The biggest one (isoform 9) has 508 amino acids while the one we used (isoform 2) has 488. Isoform 2 lacks 20 amino acids in the region called TAD (transactivation domain) compared to isoform 9. Therefore, we hypothesize that this stretch of amino acids (FIG. 3C) may also inhibit the signaling by TNFα, IL-1β, and LPS.

Figure 3D:
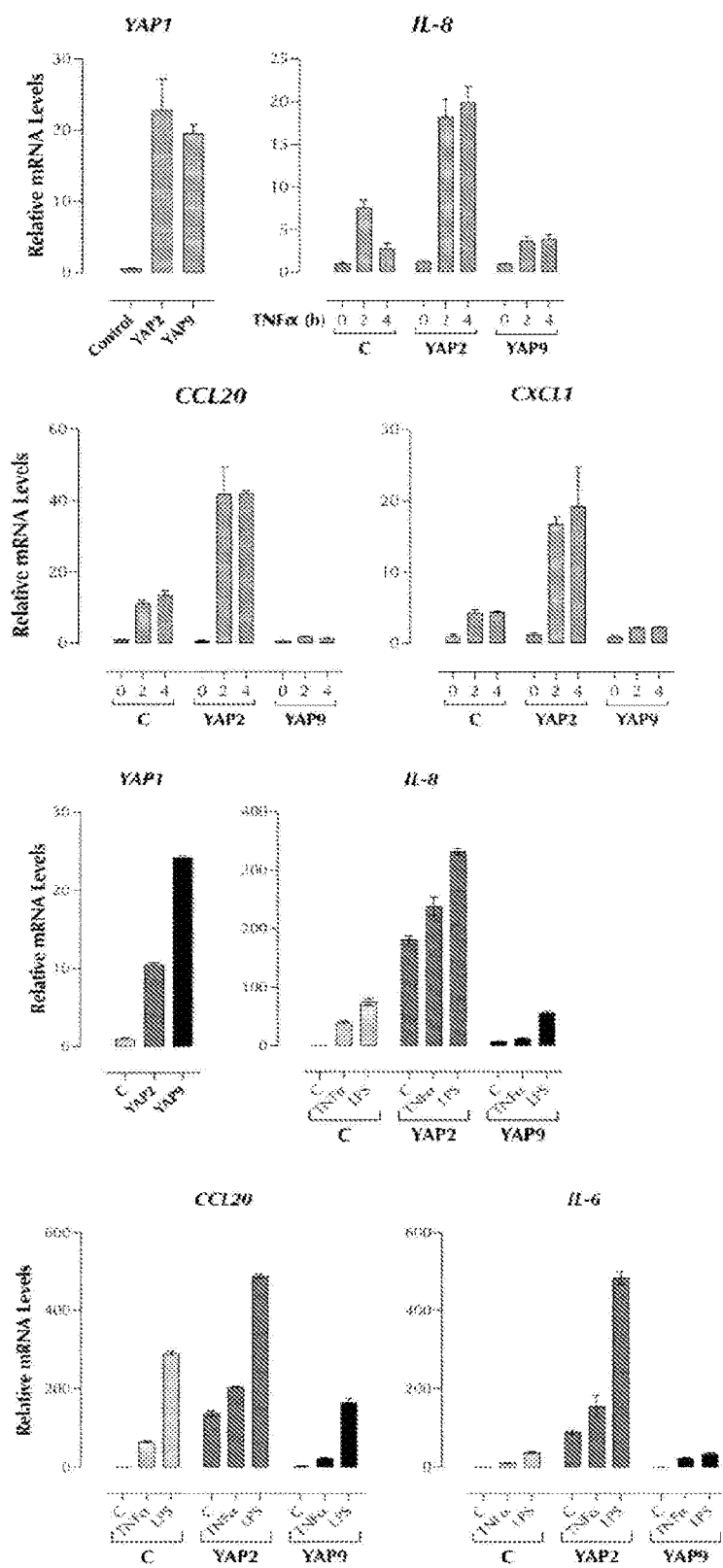
FIG. 3D shows that YAP9 suppresses the TNFα and LPS responses while YAP2 enhances them. (Top) Control, YAP2, or YAP9 plasmid was transfected to HCT-8 cells and next day the cells were stimulated with TNFα (2 ng/ml) for 4h to measure the gene expression by qPCR. (Bottom) Control, YAP2, or YAP9 plasmid was transfected to THP-1 cells and the cells were stimulated with TNF (2 ng/ml) or LPS (200 ng/ml) next day for 2h to measure the gene expression by qPCR. The results are the representative of 3 similar experiments.

As we hypothesized, YAP9 containing both PRD and the full-length TAD suppressed TNFα- and LPS-induced gene expression while YAP2 enhanced it. This data for the first demonstrated that YAP2 and YAP9 isoforms have the opposing functions in the inflammatory responses and that PRD and TAD domains play the critical role in suppression of the response to TNFα, IL-1β, and LPS (FIG. 3D).

4. PRD and TAD Peptides Inhibit Gene Expression Induced by TNFα, IL-1β, and LPS

Figure 4A:
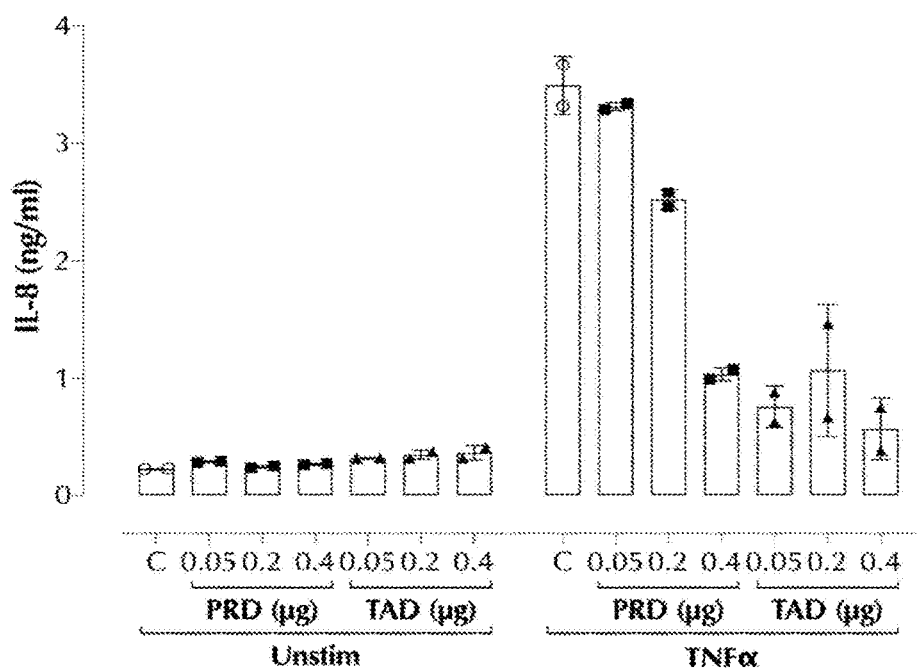
FIG. 4A shows that both PRD and TAD peptides inhibit TNFα-induced IL-8 expression in HCT-8 cells. The indicated amount of the peptides was transfected into HCT-8 as described in the method. The transfected cells were stimulated with TNFα (4 hours after peptide transfection) for 24 hours. IL-8 expression was measured by ELISA. The results are the representative of 3 similar experiments.
Figure 4B:
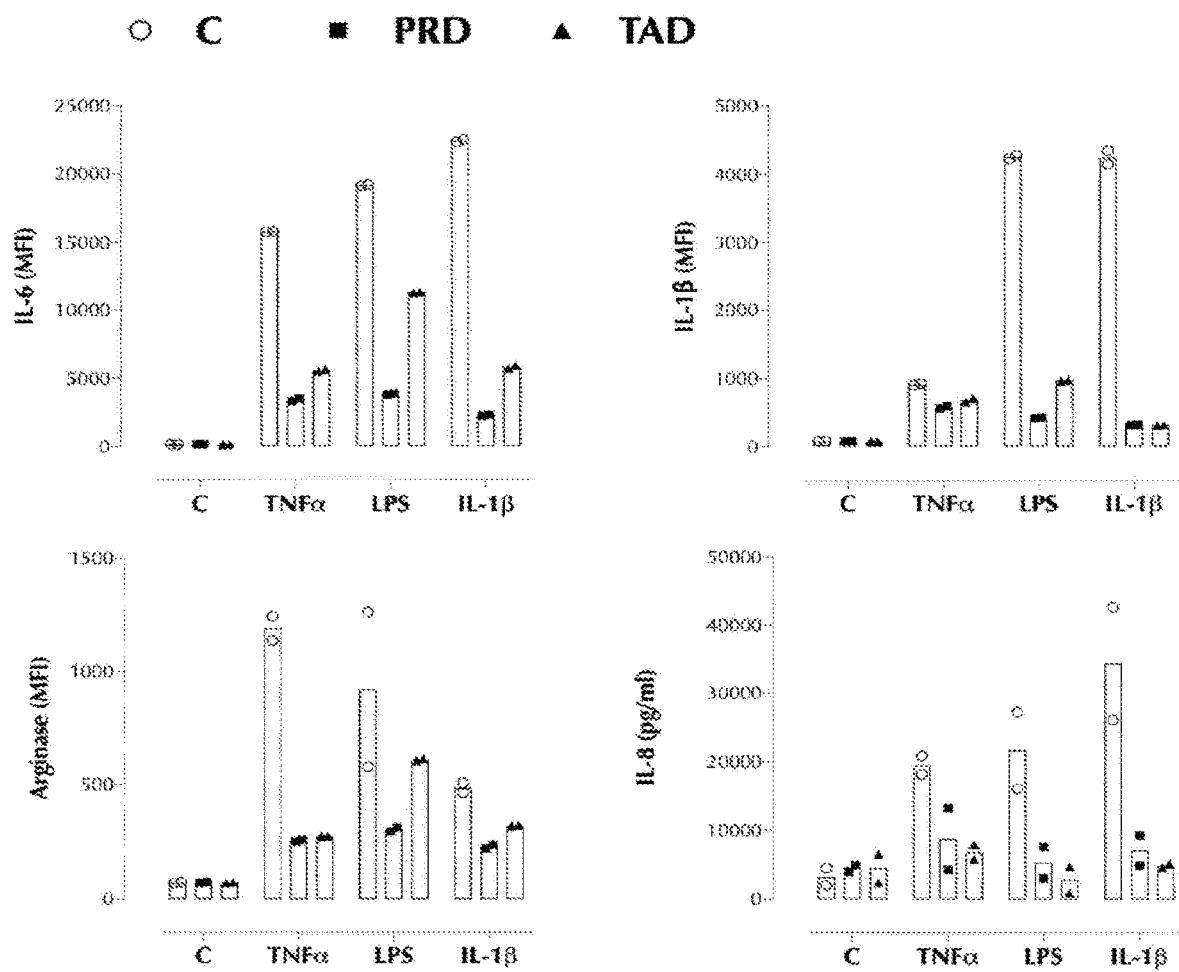
FIG. 4B shows that both PRD and TAD peptides inhibit gene expression induced by TNFα, LPS, or IL-1β in human PBMCs. PBMCs were transfected with either PRD (1 μg) or TAD (0.5 μg) as described in the method. The transfected cells were stimulated with TNFα (2 ng/ml), LPS (50 ng/ml), or IL-1β (2 ng/ml), 4 hours after peptide transfection, for 24 hours. IL-8 expression was measured by ELISA and IL-6, IL-1β, and arginase levels were measured by flow cytometry using LegendPlex as described in the method. The results are the representative of 3 similar experiments.
Figure 4C:
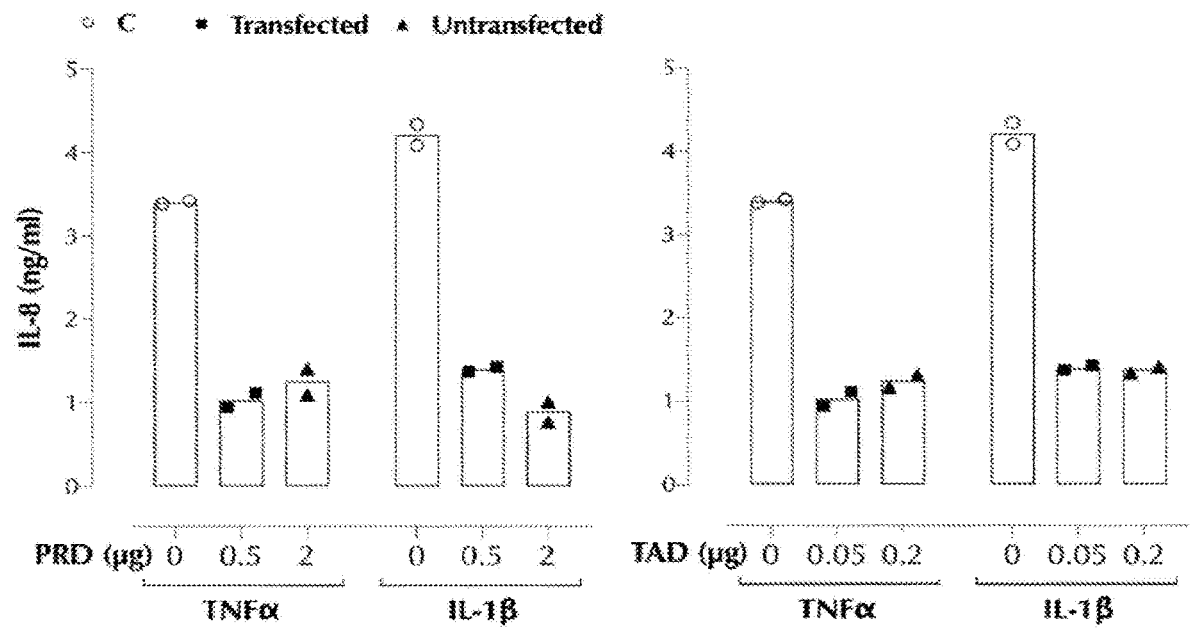
FIG. 4C shows that both PRD and TAD peptides inhibit IL-8 expression induced by TNFα or IL-1-α without transfection. HCT-8 cells were transfected with the peptides or just treated with them without transfection (1 μg/ml) and stimulated with TNFα (2 ng/ml) or IL-1-β (1 ng/ml) for 24 hours. PMBCs were treated with the indicated amount of each peptide (no transfection) and stimulated with TNFα (2 ng/ml) for 24 hours. IL-8 expression was measured by ELISA. The results are the representative of 2 similar experiments.
Figure 4C:
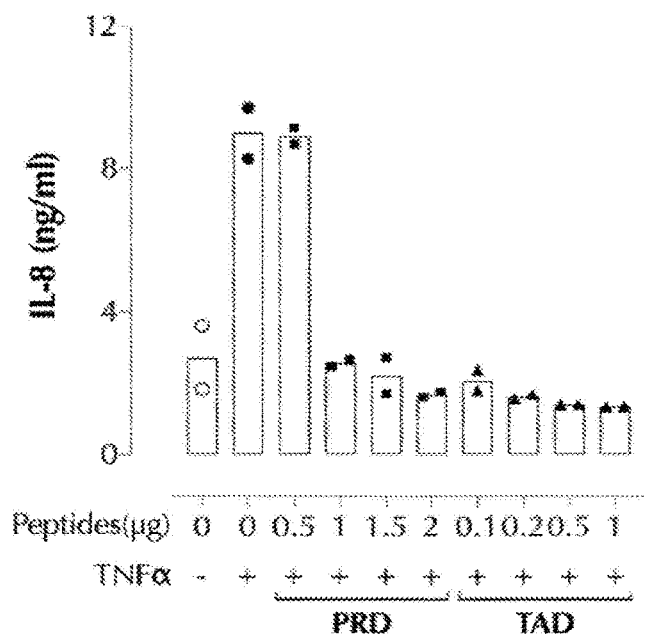

In order to test the hypotheses that the PRD and TAD peptides inhibit the response to pro-inflammatory stimuli such as TNFα, IL-1β, and LPS, the peptides were synthesized and transfected into HCT-8 cells using a protein transfection reagent (Pierce). The results show that the peptides did not affect expression of IL-8 by themselves but suppressed TNFα-induced IL-8 expression in HCT-8 cells, and TAD peptide was more potent than PRD peptide (FIG. 4A). Next, we tested whether they can inhibit the expression of genes induced by TNFα, IL-1β, and LPS in human PBMCs. Both peptides indeed inhibited the expression of IL-6, IL-1β, IL-8, and arginase induced by TNFα, IL-1β, or LPS (FIG. 4B). Since both peptides are highly hydrophobic, we tested whether they can penetrate cells. Indeed, both peptides inhibited TNFα- or IL-1β-induced IL-8 expression with or without the transfection agent in HCT-8 cells, although it took more peptides to produce the similar level of inhibition (FIG. 4C, left panel). The same was true in PBMCs (FIG. 4C, right panel). We could verify that the biotinylated PRD and TAD peptides are mostly localized in the cytoplasm of THP-1 cells (confocal imaging data not shown). In summary, our data show that both PRD and TAD peptides inhibit the gene expression induced by TNFα, IL-1β, or LPS. We tested a random peptide sequence (ARNDCEQGHILKMFPSTWYV, SEQ ID NO:41) as a control and it had no effect on the cellular response to TNFα, IL-1β, and LPS (data not shown).

Figure 4D:
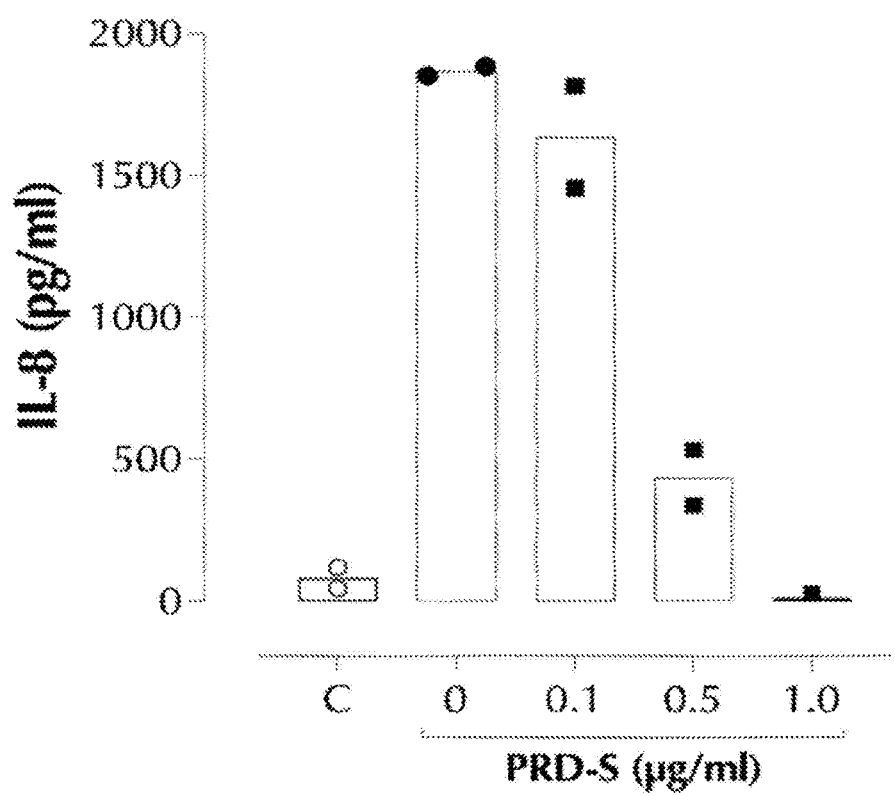
FIG. 4D shows that PRD-S peptide inhibits IL-8 expression induced by TNFα without transfection. HCT-8 cells were stimulated with TNFα (2 ng/ml) with the indicated amount of PRD-S peptide for 24 hours. IL-8 expression was measured by ELISA.

Based on the sequence analysis of the YAP1 mutants (FIG. 2A), we tested whether the shortest PRD peptide (M1) inhibits the TNFα response. We named this peptide as PRD-S(small). Indeed, PRD-S inhibited TNFα-induced IL-8 expression in a dose-response manner (FIG. 4D).

5. YAP9 Suppresses the Inflammatory Responses in Collaboration with A20 (TNFAIP3)

Figure 5A:
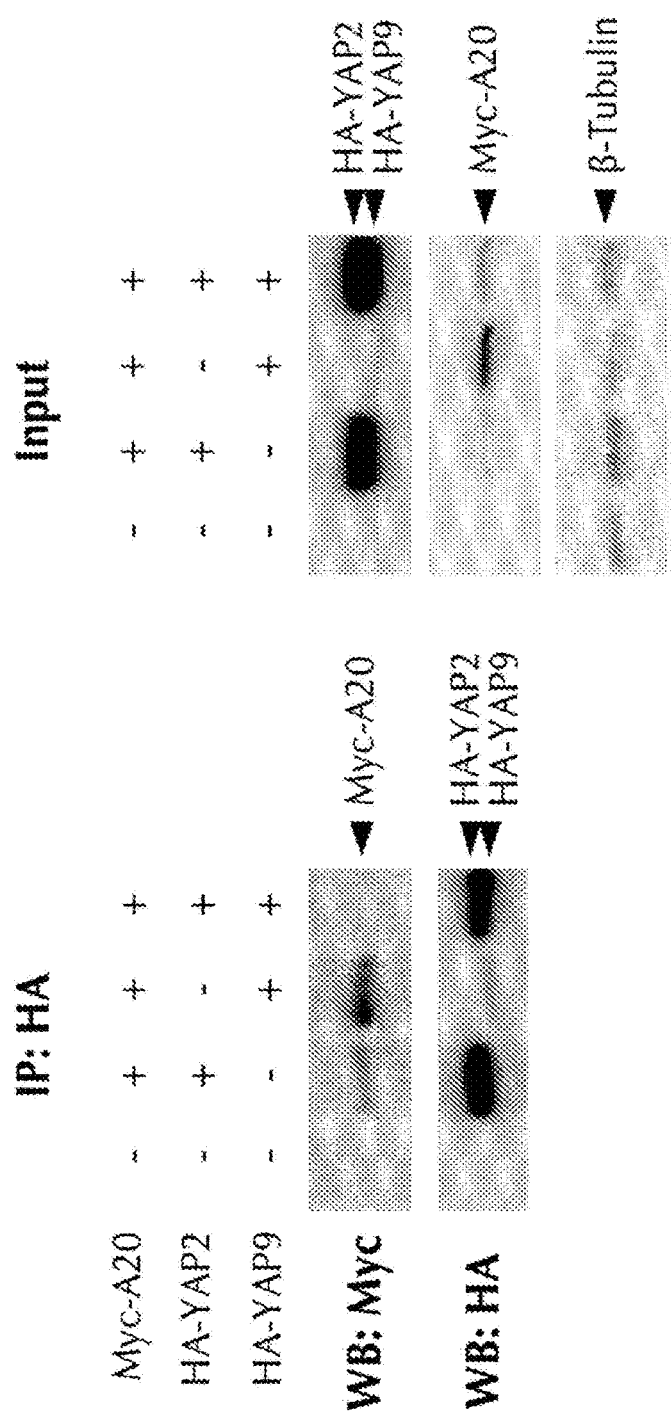
FIG. 5A shows that A20 associates with YAP9 more strongly than with YAP2. In order to test whether YAP proteins physically interact with A20, Myc-A20, HA-YAP2, and HA-YAP9 expression vectors (1 μg plasmid each) were transfected to 293-T cells as indicated. YAP proteins were pulled down with anti-HA antibody and the immunoprecipitated (IP) proteins were subjected to SDS-PAGE and western blotting (WB) as indicated. The data show that while both YAP9 binds to A20 with a higher affinity than YAP2 does. The results are the representative of 3 similar experiments.

Next, we investigated how YAP9 inhibits the cellular response to TNFα, IL-1-β, and LPS. Although these 3 stimuli share the distal signaling molecules such as NF-κB and MAP kinases, they use different signaling molecules proximal to each receptor. Therefore, we hypothesized that YAP9 must be regulating a negative signaling molecule shared by all 3 stimuli. One of the candidates is A20 also known as TNFAIP3 (TNFα-induced protein 3) that inhibits the signaling transduction by all 3 stimuli. Therefore, we tested whether YAP9 (or YAP2) physically associates with A20. Epitope-tagged Myc-A20, HA-YAP2, and HA-YAP9 were transfected to 293-T cells, and HA-YAP2 or HA-YAP9 was immunoprecipitated using anti-HA antibody. Both YAP2 and YAP9 pulled down A20 and YAP9 had a higher affinity to A20 than YAP2 since YAP9 pulled down much more A20 than YAP2 did although the YAP2 expression level was much higher than YAP9 (FIG. 5A).

Figure 5B:
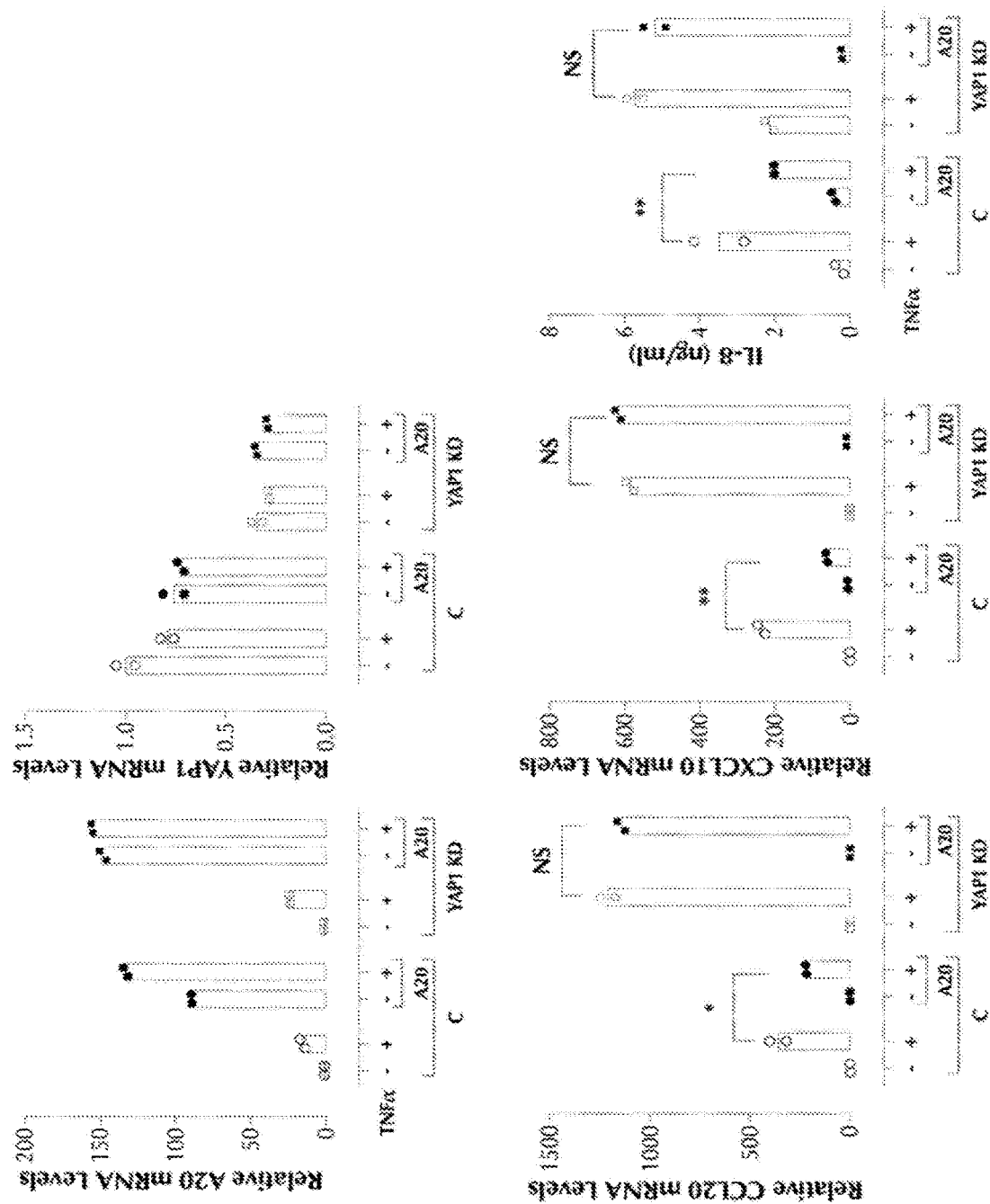
FIG. 5B shows that A20 requires YAP9 to suppress the TNFα response. A stable YAP1-KD HCT-8 cell line was created first by transfecting a YAP1 shRNA-expressing plasmid and selecting with puromycin. Myc-A20 was over-expressed in Control (C) or YAP1-KD HCT-8 cells and the TNFα response was measured by qPCR and ELISA as shown. A20 significantly suppressed the TNFα response in the C cells but not in YAP1-KD cells. YAP1 shRNA depletes all YAP isoforms. The results are the representative of 3 similar experiments.
Figure 5C:
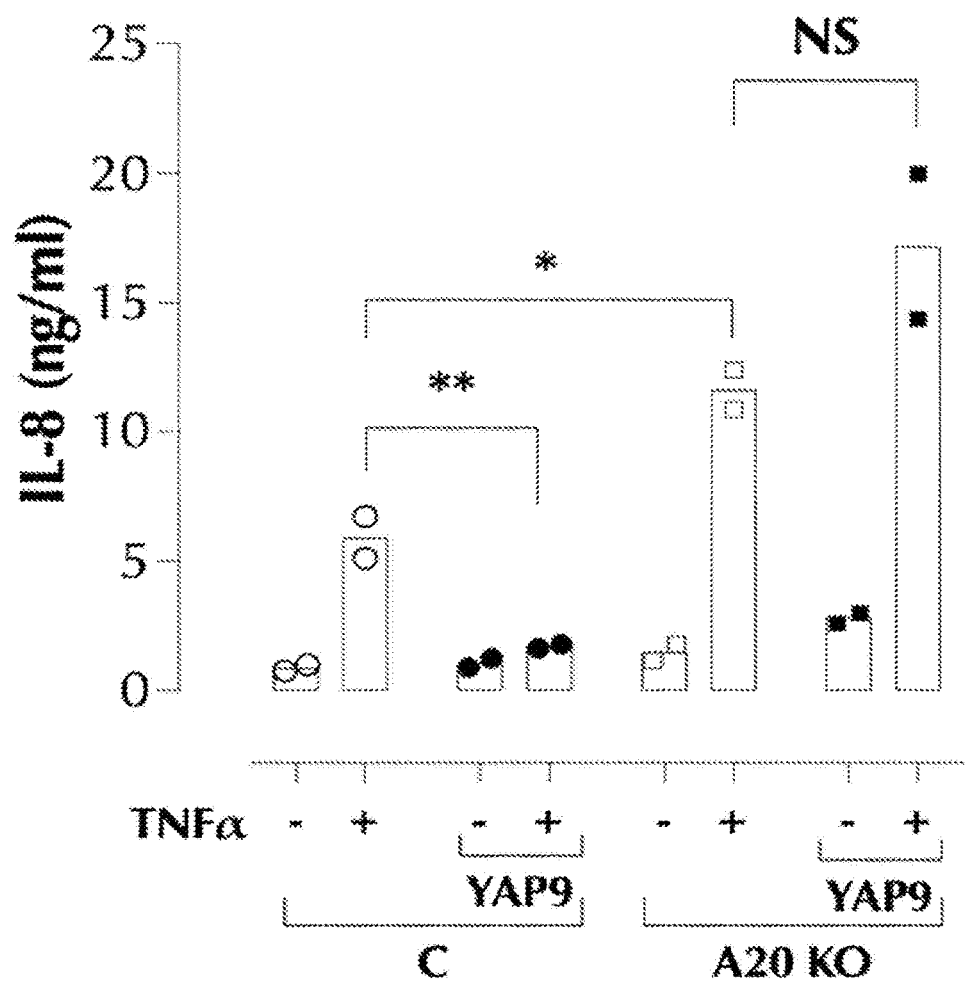
FIG. 5C shows that YAP9 requires A20 to suppress the TNFα response. A stable A20-KO HCT-8 cell line was generated using the CRISPR/Cas9 technique. HA-YAP9 was over-expressed in Control (C) or A20 KO HCT-8 cells and the TNFα response was measured by ELISA as shown. YAP9 significantly suppressed the TNFα response in the C cells but not in A20-KO cells. The results are the representative of 3 similar experiments.
Figure 5D:
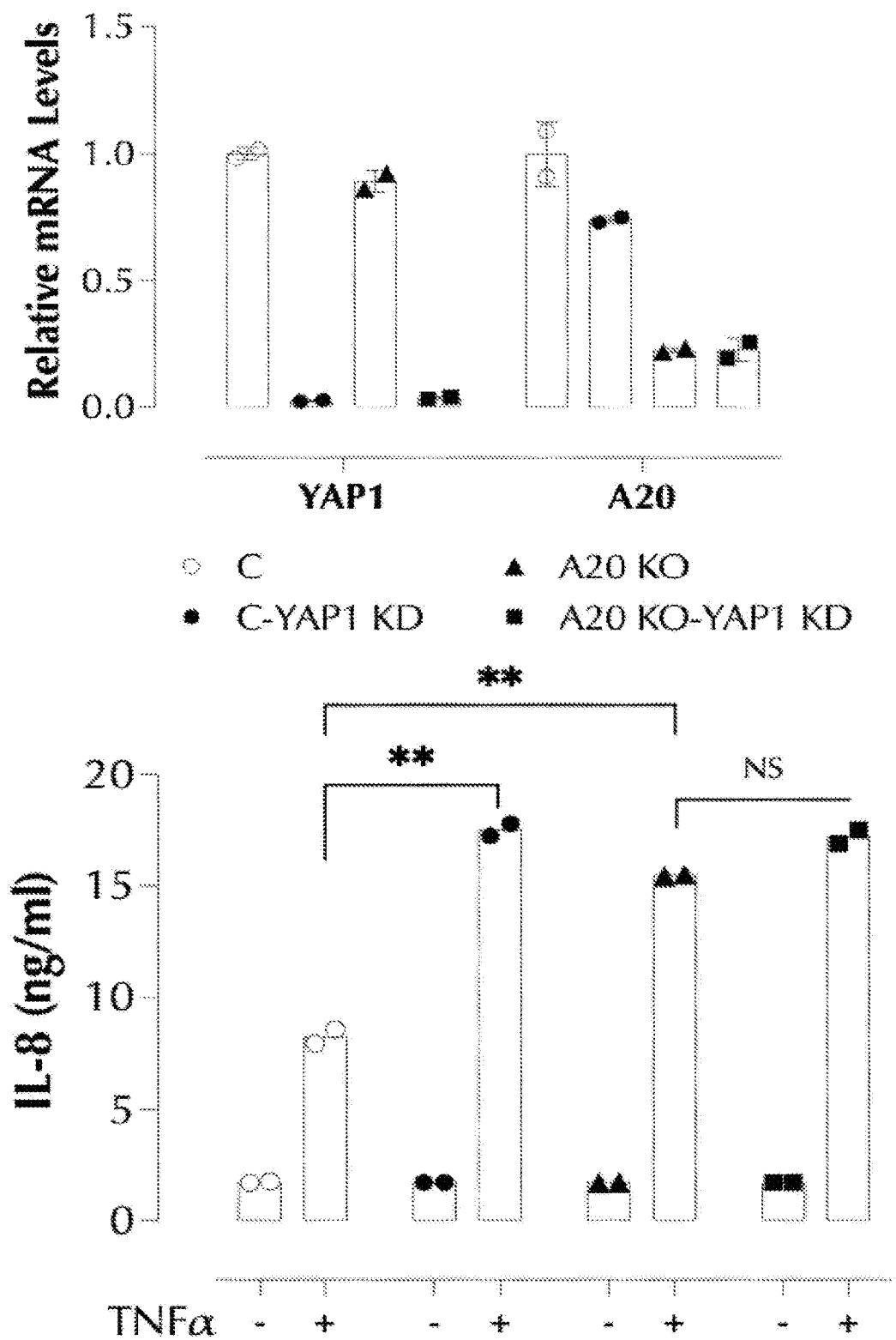
FIG. 5D shows that there is no difference in the TNFα response between the YAP1 and A20 double deficiency and the YAP1 or A20 single deficiency. YAP or/and A20 was depleted in HCT-8 cells as indicated and the cells were stimulated with TNFα (2 ng/ml) for 24h and IL-8 was measured by ELISA. Note: YAP1 siRNA depletes all YAP isoforms. The results are the representative of 2 similar experiments.

Next, we investigated whether the interaction between YAP9 and A20 is necessary for them to suppress the inflammatory responses. If they needed each other for suppression, over-expression (OE) of YAP9 should not be able to inhibit the TNFα response in the absence of A20 and similarly A20 OE should not be able to inhibit the TNFα response in the absence of YAP9. Indeed, A20 OE no longer suppressed the TNFα response when YAP1 (all isoforms) was depleted (FIG. 5B), and similarly YAP9 OE no longer suppressed the TNFα response when A20 was depleted (FIG. 5C). By the same logic, either A20 or YAP9 deficiency is enough to enhance the TNFα response and therefore A20 and YAP9 double deficiency should not further enhance the TNFα response. Our data indeed show that the TNFα response was similar between the single A20 or YAP depletion and the A20 and YAP9 double deficiency (FIG. 5D).

6. ZF7 Peptide in A20 Suppresses Inflammation In Vitro and In Vivo

Figure 6A:
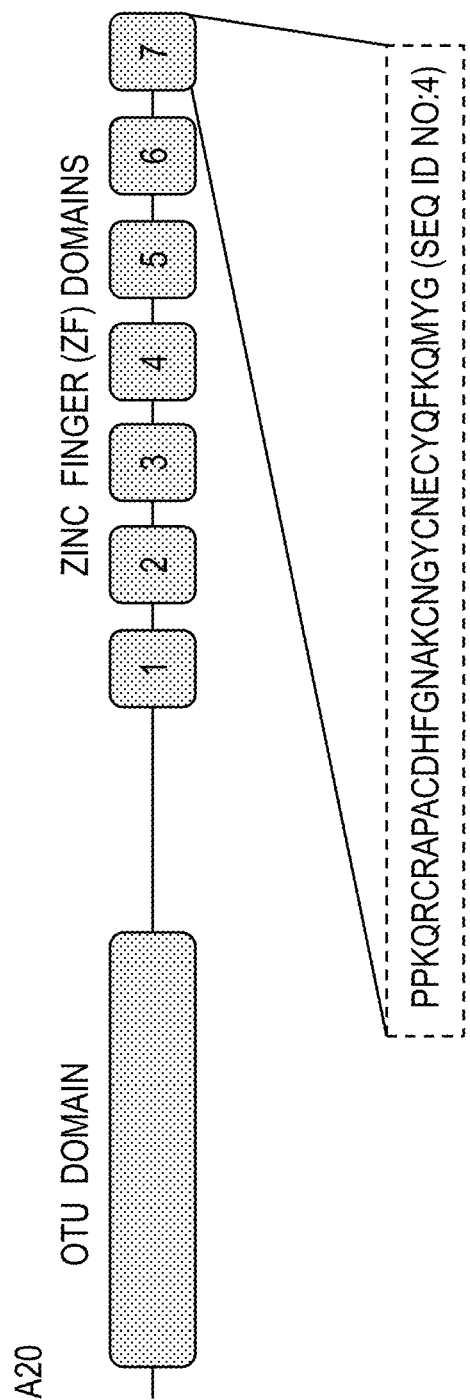
FIG. 6A shows that synthetic ZF7 peptide inhibits the TNFα response. The ZF7 peptide was either added to the medium or transfected with the protein transfection agent (OTU: Ovarian Tumor Deubiquitinase).
Figure 6B:
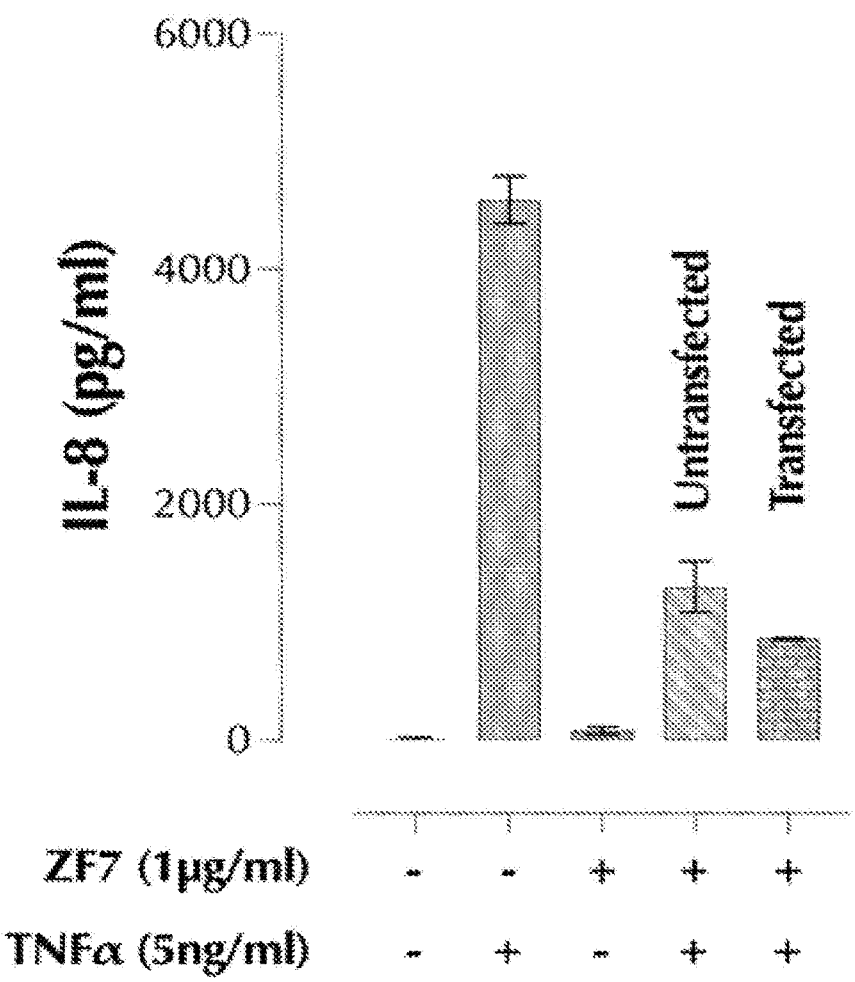
FIG. 6B shows that HCT-8 cells were stimulated with TNFα (2 ng/ml) overnight for IL-8 ELISA The results are the representative of 2 similar experiments.

Recent findings identified the ZF7 (zinc finger domain 7) as the key domain for A20 to suppress inflammation (FIG. 6A). We hypothesized that ZF7 peptide inhibit the TNFα response just as PRD and TAD peptides do. Indeed, the synthetic ZF7 significantly inhibited the TNFα response without the need of transfection in HCT-8 cells (FIG. 6B). Next, we tested whether ZF7 inhibits LPS response in vivo. We injected mice with a high dose of LPS (200 μg/mouse) or LPS+ZF7 (200 μg/mouse) and collected the sera after 3 hours. ZF7 almost completely inhibited all the cytokines and chemokines measured (Table 1). In order to tract ZF7 peptide inside cells, biotin was attached to the N-terminus to ZF7 peptide. We found that biotin did not affect the activity of PRD, TAD, or ZF7 peptide (data not shown).

Table.1 ZF7 peptide inhibits the LPS response in mice. C57BL/6 mice (n=2) were injected intraperitoneally with LPS (200 μg/mouse) or LPS (200 μg/mouse)+ZF7 peptide (200 μg/mouse) and the sera were collected after 3 hours. The cytokines and chemokines in the sera were measured by LegendPlex according to the manufacturer's instruction. The number represents pg/ml.

Figure 6C:
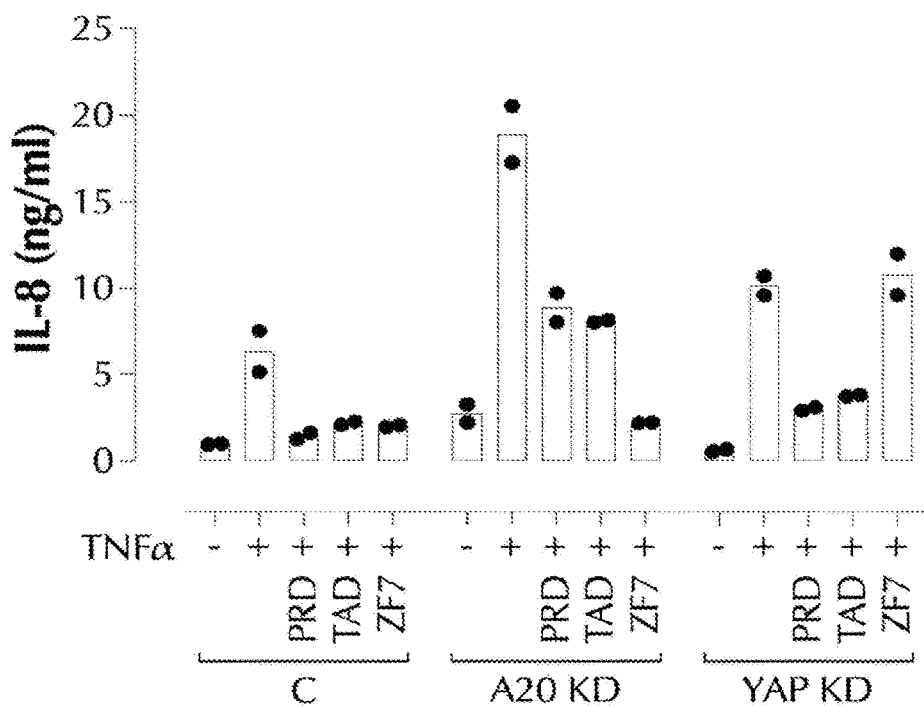
FIG. 6C shows that PRD, TAD, and ZF7 peptides mimic the effects of YAP9 and A20 OE. HCT-8 cells (C, A20 KD, YAP KD) were treated with PRD, TAD, or ZF7 peptide (1 μg/ml) and stimulated with TNFα (2 ng/ml) overnight. IL-8 levels in the medium were measured by ELISA. The results are the representative of 2 similar experiments.

Next, we investigated how PRD, TAD, and ZF7 peptides inhibit the TNFα response. The PRD, TAD, and ZF7 peptides have the same effect as either YAP9 OE (over-expression) or A20 OE, respectively. Since YAP9 OE or A20 OE is futile in the absence of the other (FIGS. 5B and 5C), PRD or TAD peptide should also require the presence of A20 while ZF7 peptide the presence of YAP9. Indeed, our data supported this notion. When both YAP9 and A20 are present (C), all 3 peptides inhibited the TNFα response. When A20 is depleted (A20 KD), PRD and TAD peptides were significantly less effective while ZF7 peptide still retained its full inhibitory capacity. When YAP is depleted (YAP KD), ZF7 peptide was ineffective while PRD or TAD peptide retained their full inhibitory capacity (FIG. 6C). These data provide the mechanism by which the YAP9-A20 complex suppresses the TNFα response.

7. ZF7 Peptide Protects Mice from Endotoxic Shock

Figure 6D:
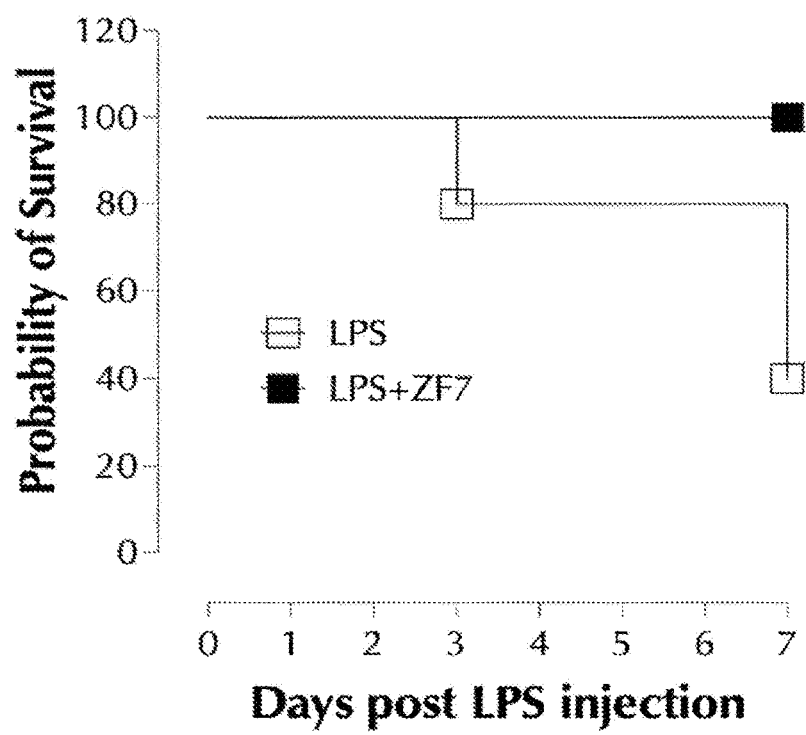
FIG. 6D shows that ZF7 protects mice from LPS-induced mortality. Mice (8-week old, C57B/6, n=5) were injected with LPS (200 μg) or LPS (200 μg)+ZF7 (300 μg) in 200 μl PBS intraperitoneally. Mortality was observed for 7 days.

Since ZF7 inhibited LPS-induced cytokine production in mice (Table 1), we next tested whether ZF7 peptide can protect mice from LPS-induced mortality. Indeed, LPS induced 60% mortality in the control group but no mortality was observed in the LPS+ZF7 group (FIG. 6D).

Figure 7A:
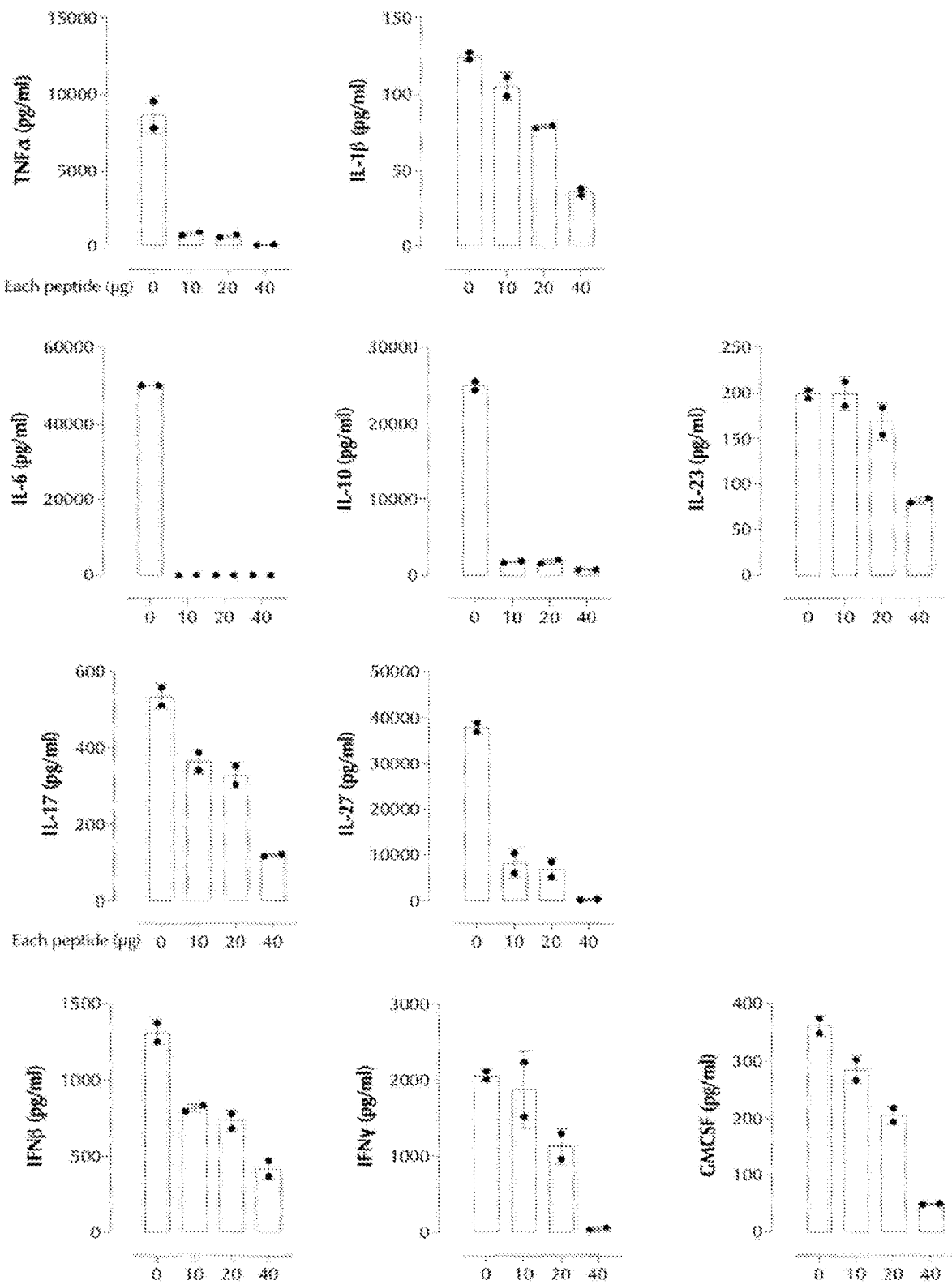
FIG. 7A shows that the combination of PRD, TAD, and ZF7 inhibits LPS-induced cytokine storm in mice. C57BL/6 mice (8-week old female) were injected i.p. with LPS or LPS with the indicated amount of the peptide combination and serum cytokines were measured 3 hours post the injection by LegendPlex.
Figure 7B:
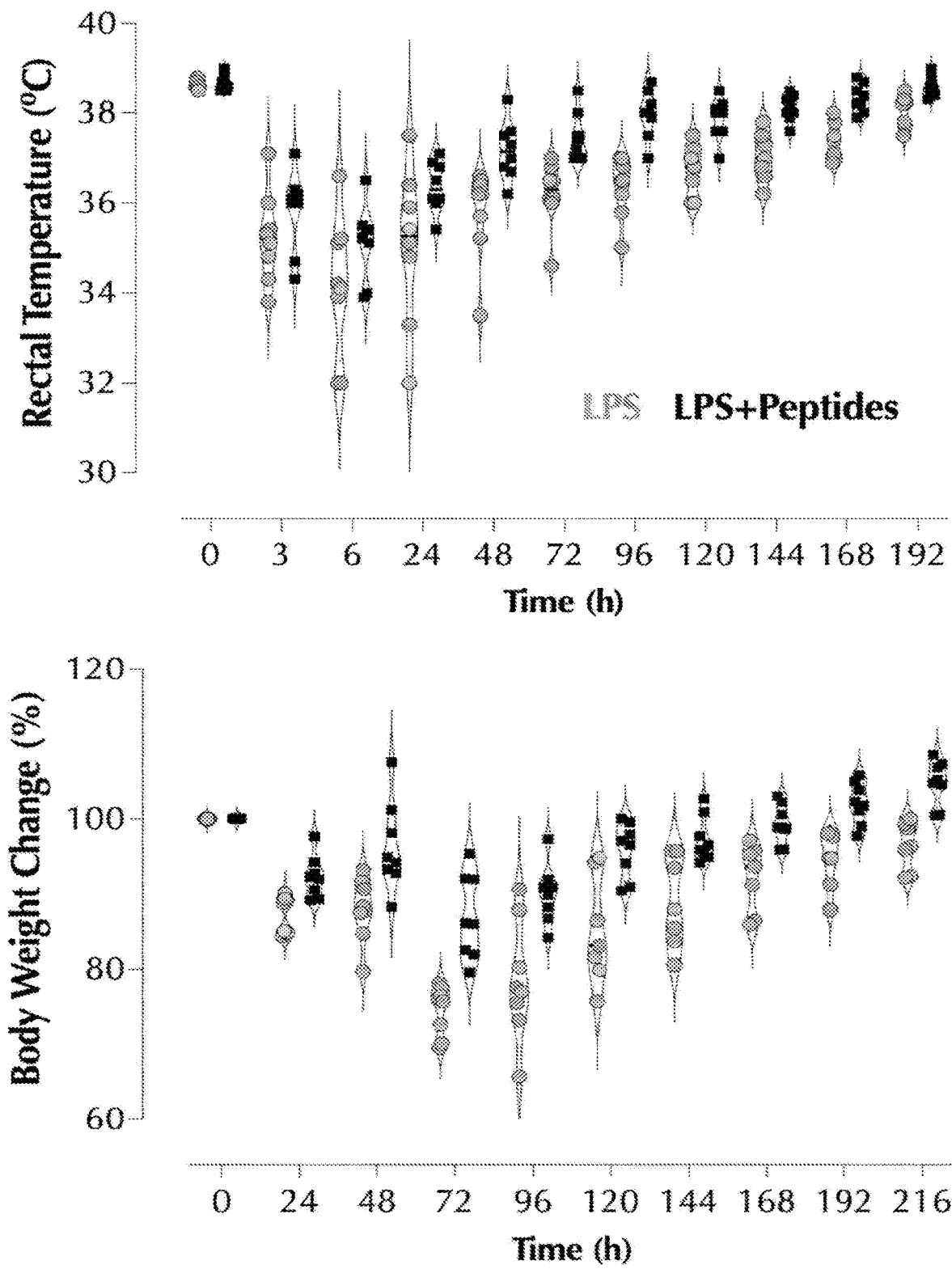
FIG. 7B shows that the combination of PRD, TAD, and ZF7 inhibits LPS-induced endotoxic shock symptoms in mice. C57BL/6 mice (8-week old female, n=8) were injected i.p. with LPS (50 μg/mouse) or LPS with the peptide combination (40 μg each peptide/mouse) and the rectal temperature and body weight change were monitored as indicated for 7 days. The peptide combination significantly inhibited hypothermia (P=0.001) and cachexia (P<0.0001). The statistical significance was calculated by 2-way ANOVA.

8. Combination of PRD, TAD, and ZF7 Peptides Inhibit LPS-Induced Cytokine Storm and Protects Mice from Endotoxic Shock We next tested the combination of the 3 peptides on LPS response in mice. Mice (n=2) were injected with a sublethal dose of LPS (50 μg/mouse) alone or LPS with different doses of the peptide combination. Sera were collected after 3 hours and cytokines were measured by LegendPlex. The data show that the combination of 40 μg of each peptide inhibited the cytokine storm almost completely (FIG. 7A).

Next, we tested if the peptide combination can alleviate the endotoxic shock symptoms in mice. The peptide combination significantly inhibited hypothermia (rectal temperature) and cachexia (body weight loss).

In summary, we found a new mechanism by which YAP1 suppresses pro-inflammatory signaling. Although YAP1 was previously reported to inhibit TNF signaling, the precise mechanism by which YAP1 inhibits TNF signaling was either not provided or a different mechanism was proposed. Because YAP1 is mainly known as a co-transcription factor, the role of YAP1 as non-transcription factor has never been described on the cellular responses to pro-inflammatory stimuli. Our data for the first time demonstrated that YAP9 (isoform 9) inhibits the signaling of pro-inflammatory stimuli as non-transcription factor and a co-factor of A20, and that it uses two specific regions to inhibit. Therefore, the PRD and TAD peptides themselves, when synthetically made, mimics YAP1 in inhibiting the signaling by the pro-inflammatory stimuli. Similarly, we describe for the first time that A20 requires YAP9 as a co-factor to suppress inflammation and that ZF7 peptide mimics the effect of the whole A20 protein in suppressing inflammation. In total, we

|  | IL-1α | IL1-β | IFNγ | IL-10 | TNFα | IL-27 | IL-17A | IFNβ | GMCSF | CCL2 | IL-6 |
|---|---|---|---|---|---|---|---|---|---|---|---|
| LPS | >1880.33 | 30.63 | 2754.30 | >1034.44 | 4998.58 | >1026.89 | >429.27 | 33.91 | 32.74 | >8082.19 | >21675.62 |
| (200 μg) | >1880.33 | 30.91 | 1801.56 | >1034.44 | 4998.58 | >1026.89 | >429.27 | 16.59 | 27.97 | >8082.19 | >21675.62 |
| LPS + ZF7 | <26.12 | <4.33 | <0.53 | <9.48 | <4.10 | <8.56 | <4.47 | <4.36 | <18.38 | 238.13 | 4142.37 |
| (200 μg) | 57.24 | 14.99 | 87.58 | 65.31 | 44.45 | 137.96 | 129.84 | <4.36 | <18.38 | 222.5 | 1570.50 | discovered 3 new anti-inflammatory peptides that alone or in a combination potentially treat various acute and chronic inflammatory diseases.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method for inhibiting a cellular response to inflammatory stimuli comprising contacting cells with a PRD peptide consisting of SEQ ID NO:1, a PRD-S peptide consisting of SEQ ID NO:2, a TAD peptide consisting of SEQ ID NO:3, a ZF7 peptide consisting of SEQ ID NO:4, or a mixture thereof.

2. The method of claim 1, wherein the cells are selected from the group consisting of fibroblasts, monocytes, human peripheral blood mononuclear cells, and epithelial cells.

3. The method of claim 1, wherein the inflammatory stimuli are selected from the group consisting of TNF-α, IL-1β and LPS.

4. The method of claim 1, wherein the PRD peptide, PRD-S peptide, TAD peptide, ZF7 peptide, or mixture thereof inhibits gene expression of inflammatory genes induced by the inflammatory stimuli.

5. The method of claim 4, wherein the inflammatory genes are selected from the group consisting of IL-6, IL-8, CXCL10, IL-32, CCL2, CCL20 and COX-2.

6. A method for treating endotoxic shock comprising administering to a subject in need thereof
    (a) a ZF7 peptide consisting of SEQ ID NO:4; or
    (b) a PRD peptide consisting of SEQ ID NO:1, a TAD peptide consisting of SEQ ID NO:3, and a ZF7 peptide consisting of SEQ ID NO:4.

7. The method of claim 6, wherein the step of administering comprises an injection.

8. A method for inhibiting or lessening a sign or symptom of a cytokine-storm-mediated disease comprising administering to a subject in need thereof a PRD peptide consisting of SEQ ID NO:1, a PRD-S peptide consisting of SEQ ID NO:2, a TAD peptide consisting of SEQ ID NO:3, a ZF7 peptide consisting of SEQ ID NO:4, or a mixture thereof.

9. The method of claim 8, wherein the cytokine-storm-mediated disease is selected from a group consisting of an autoimmune disease, a bacterial or viral infection, and a cytokine release syndrome caused by tumor immunotherapy.

10. The method of claim 9, wherein the cytokine-storm-mediated disease is selected from a group consisting of septicemia, COVID-19, inflammatory bowel disease, rheumatoid arthritis and sepsis.

11. The method of claim 8, wherein the step of administering comprises an injection.

12. The method of claim 8, wherein the sign of the cytokine-storm-mediated disease comprises expression of an inflammatory gene selected from the group consisting of TNF-α, IL-1β, IL-6, IL-10, IL-23, IL-17, IL-27, IFNβ, IFNγ, GMCSF, IL-8, CXCL10, IL-32, CCL2, CCL20, and COX-2.

13. The method of claim 8, wherein the symptom of the cytokine-storm-mediated disease comprises endotoxic shock, hypothermia, or cachexia.

* * * * *